United States Patent
Silva et al.

(10) Patent No.: US 10,603,493 B2
(45) Date of Patent: Mar. 31, 2020

(54) INTEGRATED NANOWIRE ARRAY DEVICES FOR DETECTING AND/OR APPLYING ELECTRICAL SIGNALS TO TISSUE

(71) Applicant: The Regents of the University of California, Oakland, CA (US)

(72) Inventors: Gabriel A. Silva, Del Mar, CA (US); Massoud L. Khraiche, San Diego, CA (US); Gert Cauwenberghs, San Diego, CA (US); Yu-Hwa Lo, San Diego, CA (US); William R. Freeman, Del Mar, CA (US); Sohmyung Ha, La Jolla, CA (US); Yi Jing, La Jolla, CA (US); E. J. Chichilnisky, Del Mar, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 14/419,230

(22) PCT Filed: Aug. 2, 2013

(86) PCT No.: PCT/US2013/053513
§ 371 (c)(1),
(2) Date: Feb. 2, 2015

(87) PCT Pub. No.: WO2014/022828
PCT Pub. Date: Feb. 6, 2014

(65) Prior Publication Data
US 2015/0209586 A1 Jul. 30, 2015

Related U.S. Application Data

(60) Provisional application No. 61/679,054, filed on Aug. 2, 2012, provisional application No. 61/681,656, filed
(Continued)

(51) Int. Cl.
| | | |
|---|---|---|
| A61N 1/36 | (2006.01) | |
| A61L 27/18 | (2006.01) | |
| G01N 21/64 | (2006.01) | |
| H01L 31/0352 | (2006.01) | |
| A61N 1/05 | (2006.01) | |

(52) U.S. Cl.
CPC .......... *A61N 1/36046* (2013.01); *A61L 27/18* (2013.01); *A61N 1/0543* (2013.01);
(Continued)

(58) Field of Classification Search
CPC .......................... A61N 1/36046; A61N 1/0543
See application file for complete search history.

(56) References Cited

U.S. PATENT DOCUMENTS

| | | |
|---|---|---|
| 6,038,480 A | 3/2000 | Hrdlicka et al. |
| 6,389,317 B1 | 5/2002 | Chow et al. |

(Continued)

FOREIGN PATENT DOCUMENTS

| | | |
|---|---|---|
| WO | 2001074444 A1 | 10/2001 |
| WO | 2009067668 A1 | 5/2009 |
| WO | 2011163262 A2 | 12/2011 |

OTHER PUBLICATIONS

Dayeh, S.A., et al., "Advances in the synthesis of InAs and GaAs nanowires for electronic applications", Nano Today, Jul. 5, 2009, vol. 4, pp. 347-358.
(Continued)

*Primary Examiner* — Joseph M Dietrich
(74) *Attorney, Agent, or Firm* — Eleanor Musick; Musick Davison LLP

(57) ABSTRACT

An integrated nanowire device includes a first array of nanowires having a first set of characteristics and a second array of nanowires having a second set of characteristics. A processor is electrical communication with the first and second arrays of nanowires receives the first plurality of charges and generate a processor signal therefrom. The
(Continued)

second array of nanowires may be configured to produce a stimulation current in response to the processor signal. The first or second array may be used to generate power for operation of the device, or the arrays may function as a stimulator, sensor combination to enable the device to self-regulate based on localized responses to stimulation. The device may be implanted for use as a neural stimulator.

19 Claims, 17 Drawing Sheets

Related U.S. Application Data on Aug. 10, 2012, provisional application No. 61/779,550, filed on Mar. 13, 2013, provisional application No. 61/779,680, filed on Mar. 13, 2013, provisional application No. 61/780,515, filed on Mar. 13, 2013.

(52) U.S. Cl.
CPC . *G01N 21/6456* (2013.01); *H01L 31/035227* (2013.01); *A61L 2400/12* (2013.01); *A61L 2430/16* (2013.01)

(56) References Cited

U.S. PATENT DOCUMENTS

| | | | |
|---|---|---|---|
| 7,006,873 | B2 | 2/2006 | Chow et al. |
| 7,139,612 | B2 | 11/2006 | Chow et al. |
| 7,494,840 | B2 | 2/2009 | Zhang et al. |
| 8,000,000 | B2 | 8/2011 | Greenberg et al. |
| 2002/0074227 | A1 | 6/2002 | Nisch et al. |
| 2002/0161417 | A1 | 10/2002 | Scribner |
| 2003/0032946 | A1 | 2/2003 | Fishman et al. |
| 2008/0288067 | A1 | 11/2008 | Flood |
| 2010/0106259 | A1 | 4/2010 | Linas et al. |
| 2010/0160994 | A1* | 6/2010 | Feldman ............ A61N 1/056 607/33 |
| 2012/0145880 | A1 | 6/2012 | Wober |
| 2012/0209344 | A1* | 8/2012 | Rossi ............ A61N 1/00 607/22 |
| 2013/0333094 | A1* | 12/2013 | Rogers ............ A61B 5/01 2/161.7 |
| 2014/0128972 | A1 | 5/2014 | Khraiche et al. |

OTHER PUBLICATIONS

Dayeh, S.A., et al., "Integration of vertical InAs nanowire arrays on insulator-on-silicon for electrical isolation", Applied Physics Letters, Nov. 20, 2008, vol. 93, 203109-1 to 203109-3.

Fan, Z., et al., "Large-scale, heterogeneous integration of nanowire arrays for image sensor circuitry", PNAS, Aug. 12, 2008, vol. 105, No. 32, pp. 11066-11070.

Kim, H., et al., "Fabrication of Vertical Silicon Nanowire Photodetector Arrays using Nanoimprint Lithography", Advanced Fabrication Technologies for Micro/Nano Optics and Photonics III, ed. Schoenfeld, W.V. et al., Proc. of SPIE, 2010, vol. 7591, 759106-1 to 759106-7.

Okugawa, A., et al., "Heterogeneous Integration of Vapor-liquid-solid Grown Silicon Microprobe Arrays (111) and MOSFETS (100) using Silicon on Insulator Substrate", Proceedings of the IEEE Micro Electro Mechanical Systems (IEEE-MEMS) Conference 2010, Hong Kong, Jan. 2010, pp. 372-375.

Silva, G.A., "Neuroscience nanotechnology: progress, opportunities and challenges", Nature Reviews Neuroscience, Jan. 2006, vol. 7, pp. 65-74.

Soci, C., et al., "Nanowire Photodetectors", Journal of Nanoscience and Nanotechnology, 2010, vol. 10, pp. 1-20.

Sun, K., et al., "Compound Semiconductor Nanowire Solar Cells", IEEE Journal of Selected Topics in Quantum Electronics, 2011, 17(4), pp. 1033-1049.

Wei, W., et al., Direct Heteroepitaxy of Vertical InAs Nanowires on Si Substrates for Broad Band Photovoltaics and Photodetection, Nano Letters, 2009, vol. 9, No. 8, pp. 2926-2934.

Xiang, B., et al., "Rational Synthesis of p-Type Zinc Oxide Nanowire Arrays Using Simple Chemical Vapor Deposition", Nano Letters, 2007, vol. 7, No. 2, pp. 323-328.

Zhang, A., et al., "Silicon nanowire detectors showing phototransistive gain", Applied Physics Letters, 2008, vol. 93, 121110-1 to 121110-3.

EP 11798773.5 Extended European Search Report, dated Nov. 11, 2013, 5 pages.

PCT/US2011/041293 International Search Report and Written Opinion, dated Feb. 28, 2012, 10 pages.

PCT/US2013/053513 International Search Report and Written Opinion, dated Nov. 1, 2013, 11 pages.

Mao, P., et al., "Fabrication and characterization of 20 nm planar nanofluidic channels by glass-glass and glass-silicon bonding", Lab Chip, 2005, 5, pp. 837-844.

Nirenberg, S., et al., "Retinal prosthetic strategy with the capacity to restore normal vision", PNAS, vol. 109, No. 37, Sep. 11, 2012, pp. 15012-15017.

Raychaudhuri, S., et al., "Precise semiconductor nanowire placement through dielectrophoresis", Nano Letters 2009, vol. 9, No. 6, pp. 2260-2266.

Theogarajan, L., et al. "Visual prostheses: Current progress and challenges", VLSI Design, Automation and Test, 2009, VLSI-DAT '09, International Symposium on. 2009. pp. 126-129.

Extended European Search Report for EP13825403, dated Mar. 15, 2016, 6 pages.

\* cited by examiner

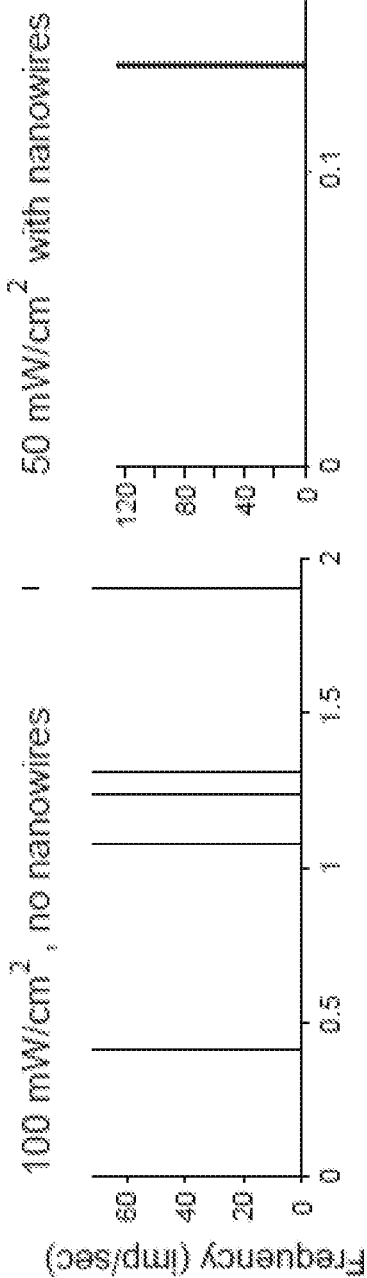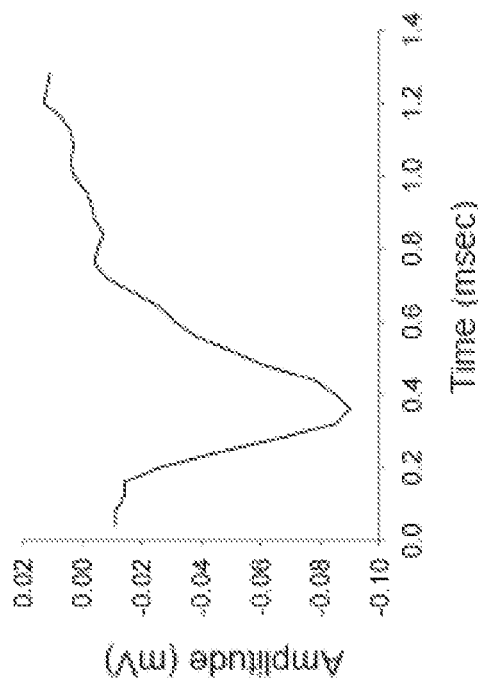

INTEGRATED NANOWIRE ARRAY DEVICES FOR DETECTING AND/OR APPLYING ELECTRICAL SIGNALS TO TISSUE

RELATED APPLICATIONS

This application is a '371 national stage filing of International Application No. PCT/US2013/053513, filed 2 Aug. 2013, which claims the benefit of the priority of U.S. Provisional Applications No. 61/679,054, filed Aug. 2, 2012, No. 61/681,656, filed Aug. 10, 2012, and No. 61/779,550, No. 61/779,680, and 61/780,515, each filed Mar. 13, 2013.

For U.S. national stage purposes, this application is a continuation-in-part of U.S. application Ser. No. 13/806,089, filed Jun. 19, 2013, which is a Rule 371 national stage filing of International Application No. PCT/US2011/041293, which claims the priority of U.S. Provisional Application No. 61/356,655, filed Jun. 21, 2010. The disclosure of each of the listed applications is incorporated herein by reference in its entirety.

FIELD OF THE INVENTION

The present invention is directed to a device for detecting electrical signals using one or more nanowires and/or generating a stimulating current using one or more nanowires.

BACKGROUND OF THE INVENTION

Degenerative disorders of the sensory retina can have a devastating impact on quality of life with significant socio-economic consequences. About 1 million people in the United States alone suffer profound vision loss, with another 2.4 million having some degree of visual impairment. As the U.S. population continues to age, it is likely that the total number of affected individuals will increase, possibly by up to 50% by 2020, especially given the dramatic rise in type II diabetes. Attempts to treat these disorders by slowing the rate of degeneration and reversing the resultant loss of vision have included genetic, pharmacological, surgical, and cellular interventions, such as the use of stem cell therapy. While these treatments offer some promise, they also face numerous challenges that have blocked some of the most promising therapies from general clinical acceptance. One exception if anti-vascular endothelial growth factor (VEGF) therapy, however, it only treats one form of late stage age-related macular degeneration, and many patients still are unable to attain driving-level vision. Some forms of neural blindness, such as retinitis pigmentosa and Stargardt disease, cannot currently be treated by any available means.

A number of projects have been undertaken to develop a retinal implant capable of restoring vision to patients suffering retinal diseases. Retinal, conical and optic nerve visual prostheses use microfabricated electronic components that can be surgically implanted to replace the lost photo-receptor (PR) neurons. Two primary sites of stimulation and surgical implantation have been explored: subretinally, with the device implanted in the space where photoreceptors used to be, or epiretinally, directly stimulating the ganglion cells. Retinal prostheses do not generally have the potentially irreversible side effects of some molecular and biological therapeutic approaches, which can include formation of tumors. In addition, with well-established surgical methods for implanting retinal prostheses, implants can be removed if needed. Nonetheless, in spite of decades of research, visual prostheses have not advanced beyond early clinical trials and have not yet produced a level of vision that has been demonstrated to improve the ability of patients to perform visual tasks related to daily activities. Existing devices are subject to serious limitations in their ability to reach appropriate electrode densities and stimulation resolutions. These limitations are largely due to the dependence on microelectrode technologies, which goes beyond the size of the microelectrodes themselves, because each electrode must be individually addressed and interconnected so it can receive injected current from the photosensing part of the prosthesis, which is separate from the microelectrode array itself. Microelectrode devices must first detect light, possibly with an external camera or microphotodiode array then determine the amount of current to be injected into each microelectrode using on-board processing. This circuitry consumes considerable space, so while the photosensing element, e.g., CCD camera, may have extremely high resolution, there is a physical limitation to the density of stimulation and, hence, the overall resolution of the device will be limited.

One example of microelectrode technology is the FDA-approved ARGUS® II (Second Sight Medical Products. Inc. (Sylmar, Calif.)) epiretinal device, which exhibits a best acuity of 20/1260 with 60 electrodes. The number of electrodes that would be needed to yield significant levels of visual acuity has been estimated to be within the range of 256 to 625 electrodes, which theoretically might yield best visual acuity of 20/240 and 20/30, respectively. The high density of ganglion cells in the retina suggests that a greater number of stimulating electrodes could be implanted in a given area, however, the number of electrodes required depends on the ability of the materials to safely transmit charge and on the proximity of the target tissue to those electrodes.

Neural and muscular stimulators used in implants and prosthetic devices such as retinal implants, cochlear implants, and cardiac pacemakers, among others, deliver electrical current, usually from a conventional current source, to tissue. Many of these devices rely on wireless power transmission from an external power supply, requiring complex circuitry for power telemetry, data telemetry, power management, clock recovery, digital control, and driving stimulation pulse. The current sources rely on a significant voltage drop across a transistor to maintain a constant current, and draw current from large DC voltage supplies, consuming relatively high levels of power for each electrode. The required power generated during stimulation is generates heat which results in damage to the surrounding tissue. Tissue such as the retina is particularly sensitive to temperature-induced damage. As described above, it is estimated that in order to obtain the desired resolution, the number of electrodes in a retinal implant will be in the hundreds to thousands. In addition to increasing heat dissipation of the stimulator, higher power consumption also exposes the surrounding tissue to larger magnetic fields due to the demand for high power transmission from the external battery power supply. Several factors that determine power consumption may be beyond the control of the designer, including the threshold for perception or function, electrode size or material.

For many reasons, including the challenges described above, the barriers to restoring vision to the blind are significant. In addition to biomaterial issues such as toxicity, tissue encapsulation and cellular/immune responses that might be triggered by foreign materials, an electrical prosthesis must also provide long-term stability of the metal electrodes while minimizing any tissue damage that occurs as a result of the electrical stimulation. Induced tissue damage will reduce the excitability of the tissue and limit the potential for vision restoration. The potential biocompatibility and long-term functional stability of a retinal prosthesis are further complicated by ongoing anatomical and physiological changes that inevitably occur within the retina in patients with retinitis pigmentosa, the primary disease that has been targeted by early visual prosthetic implantations.

A field that shows promise in overcoming the limitations of existing microelectrode-based implants is nanotechnology. As is known in the art, when particles of materials have dimensions of around 1-10 µm, the particles' properties and behavior are dominated by quantum effects. As used herein, a "nanomaterial" is a material in which quantum effects rule the behavior and properties of particles. When particle size is in the nanoscale range, properties such as melting point, fluorescence, electrical conductivity, magnetic permeability, and chemical reactivity change as a function of the size of the particle. As used herein, a "nanodevice" is a device formed from nanomaterials. Nanodevices and nanomaterials can interact with biological systems at fundamental molecular levels. By taking advantage of this unique molecular specificity, these nanotechnologies can stimulate, respond to and interact with target cells and tissues in controlled ways to induce desired physiological responses, while minimizing undesirable effects.

Nanowires have been shown to function as phototransistors with a high degree of sensitivity. Due to the small lateral dimensions (100's of nanometers to 10's of microns) and large surface-to-volume ratio of silicon (Si) nanowires, the large number of states at a Si surface can trap carriers at the surface equivalent to a gate bias, resulting in phototransistive behavior that leads to high sensitivity. This unique property of Si nanowires makes these devices attractive for photodetection from ultraviolet to the near infrared. Zhang, A., et al. ("Silicon Nanowire Detectors Showing Phototransistive Gain", *Applied Physics Letters*, 2008, Vol. 93, 121110 (−1 to −3) have shown that etched planar and vertical Si nanowires function effectively with gains exceeding 35,000 under low intensity UV illumination, demonstrating their potential for low light detection. The vertical Si nanowires in particular are effective at overcoming low physical fill factor (FF) limitations due to their strong waveguiding effects, which cause a large fraction of the photon energy to be funneled into the nanowires.

SUMMARY OF THE INVENTION

According to the invention, silicon nanowire arrays are integrated with processing circuitry and a power source to provide a sensor for detecting a stimulus and/or a stimulator that may be used for stimulating a tissue or cell. When incorporated into a retinal implant, the integrated device provides an effective replacement for photoreceptors due to near single photon sensitivity as well as the ability to tailor the size and spatial distribution of the nanowire arrays to mimic the natural retina. Nanowire devices constructed according to the present invention may be configured to perform phototransduction, power generation, recording, or stimulation, or any combination thereof, with each of the functions exploiting the versatility of nanowire arrays.

In general, the integrated nanowire device of the present invention includes a first array of nanowires having a first set of characteristics and at least one second array of nanowires having a second set of characteristics. A processor is in electrical communication with the first and second arrays of nanowires receives the first plurality of charges and generate a processor signal therefrom. The second array of nanowires may be configured to produce a stimulation current in response to the processor signal. The first or second array may be used to generate power for operation of the device, or the arrays may function as a stimulator, sensor combination to enable the device to self-regulate based on localized responses to stimulation. The device may be implanted for use as a neural stimulator.

In an exemplary embodiment, the device is based on the photonic nanowire technology described in, among other publications, WIPO Patent Publication No. WO2011/163262, which is incorporated herein by reference. The integrated nanowire array devices may be used to support the simultaneous electrical stimulation and recording of neural activities from ganglion cells in vitro and in vivo. This device may include integrated processing circuitry in communication with the nanowire arrays to execute processing functions to support the implementation of algorithms for mapping the spatial distribution of surviving ganglion cells in the neural retinas of patients with degenerative retinal disorders, leading to more precise activation of ganglion cells in an epiretinal prosthesis device. More broadly and beyond a retinal prosthesis, the invention provides for the integration of multiplexed photonic nanowire arrays that carry out different sensing, power, and energy functions, which may be integrated with circuitry configured to perform additional processing and/or to provide a self-powering multiplexed sensor device for a variety of biological and non-biological applications.

The nanowire arrays may be fabricated to include nanowires of two or more different dimensions, i.e., diameters and/or lengths, to provide the ability to detect optical signals within different wavelength ranges and at different efficiencies. Devices fabricated with silicon nanowires according to the processes disclosed in International Publication No. WO2011/163262 respond from about 300 nm to about 1700 nm, exceeding the normal range of human vision, which covers a range of around 400 nm to 700 nm. In one example, three distinct nanowire diameters may be used to simulate the three types of human cones—L (long (564-580 nm peak)—red), M (medium (534-545 nm peak)—green) and S (short (420-440 nm peak)—blue)—to provide the basis for a retinal prosthesis that enables high-resolution color vision. Other combinations of spectral responsivity may be used depending on the application. For example, infrared or ultraviolet ranges may be included. The different diameter nanowires may be fabricated within a single array, or two or more separate arrays may be combined into a single device, where each array is tuned during fabrication to a selected wavelength range. Additional variation in the nanowire behavior may be achieved through control of length, pitch and density during the fabrication process.

In one aspect of the invention, at least one optoelectronic nanowire sensor may include a receptive field sensor in the form of an additional nanowire array adapted for detecting an external input, at least one optoelectronic nanowire stimulator adapted for stimulating a localized area, and one or more integrated circuits with a processor in electrical communication with the optoelectronic nanowire sensor and the optoelectronic nanowire stimulator. Such devices may be used to self-regulate their operation by using the additional phototransduction nanowire array to detect cell responses to stimulation to allow measurement of the cells' receptive field, the data from which may be used to determine appropriate parameters for stimulating ganglion cells in the vicinity of the stimulus. The device processor may include programming to implement algorithms for processing the measured response information from, and ultimately stimulate, nearby cells. By applying appropriate algorithm(s), the inventive device is able to stimulate the cells in a manner that approximates the natural visual signals that are normally transmitted to the brain.

In some embodiments, the device may be powered by a small battery such as those used in hearing aids. However, in a preferred embodiment, the device may be self-powered by including one or more optoelectronic nanowire batteries, in which one or more nanowire arrays may be used to accumulate and store charge, taking advantage of the large surface-to-volume ratio of the nanowires to efficiently convert energy from an external source into charge. These "power arrays" may optionally be connected to one or more p-n junctions where a voltage drop is produced. The charge current that accumulates within the depletion region of the p-n junction when energy, e.g., from light, impinges on the nanowire array can be funneled from the substrate as needed and driven and gated by a bias voltage. Increasing the number of p-n junctions in series will increase the voltage drop, and a bias may be applied based on values determined by the device processor. The external source of the energy that is collected and stored as a charge in the nanowire power array may be in the form of an optical, electrical, chemical, thermal, acoustic, or other stimulus, any combination thereof.

As another option for powering an implanted device, the present invention may employ a stimulation circuit that wirelessly produces a current appropriate for neural stimulation. The stimulation circuit includes an LC resonant tank circuit and a diode. Using this approach, a stimulation electrode may be coupled directly to the inductor coil pair, using the train of sine wave pulses that are received directly from the external primary coil inductor to produce a stimulating current that is capable of eliciting action potential in neurons.

The inventive nanowire array and supporting circuitry may be embedded into a flexible adhesive biocompatible polymer system to enhance post-surgical stability of an implant incorporating the inventive device. The material of the flexible substrate may also be selected to make a device incorporating the nanowire assembly chemically stable for applications that may require exposure to harsh or hazardous environmental conditions.

In one aspect of the invention, an integrated nanowire device is provided which includes a first array of nanowires having a first set of characteristics, wherein the characteristics are selected from the group consisting of doping, spatial distribution, quantity, density, pitch, diameter, length and shape, and wherein the first array is adapted to generate a first plurality of charges in response to energy impinging thereon; at least one second array of nanowires having one or more second sets of characteristics; a processor in electrical communication with the first array of nanowires and the at least one second array of nanowires, wherein the processor is adapted to receive the first plurality of charges and generate a processor signal therefrom; and a power source. The at least one second array of nanowires may be configured to produce a stimulation current in response to the processor signal. The at least one second array of nanowires may comprises two arrays, wherein one of the two arrays is adapted to produce a stimulation current in response to the processor signal and the second of the two arrays is adapted to detect a localized response to the stimulation current and provide feedback to the processor. The processor may be programmed to execute an algorithm for receiving the feedback and adjusting the stimulation current based on the localized response, where the algorithm is based on a model for predicting retinal ganglion cell responses. In one embodiment, the model is a generalized linear model.

In some variations, the one or more second sets of characteristics will be different from the first set of characteristics so that the one or more second nanowire arrays will be optimized for different wavelength ranges and/or different responsivities or quantum efficiencies from the first nanowire array. For example, the first wavelength range may correspond to a red light range and two second nanowire arrays have two different wavelength ranges corresponding to a green light range and a blue light range.

The at least one second array of nanowires may be configured as a power array adapted to act as the power source. The power array may be fabricated on a substrate comprising one or more p-n-junctions, where each p-n junction comprises a voltage drop adapted to accumulate charges for operation of the device. A separate substrate may be provided with one or more separate p-n junctions in electrical communication with the power array. The surface of the separate substrate may be adapted to collect energy from an external energy source and generate charges therefrom.

In another aspect of the invention, an integrated nanowire device includes one or more first nanowires having a first set of characteristics, where the characteristics are selected from the group consisting of doping, spatial distribution, quantity, density, pitch, diameter, length and shape, and wherein the one or more first nanowires are adapted to generate a first plurality of charges in response to an external energy impinging thereon; one or more second nanowires having one or more second sets of characteristics, the one or more second nanowires being adapted to generate a stimulation current; a processor in electrical communication with the one or more first nanowires and the one or more second nanowires, wherein the processor is adapted to receive the first plurality of charges and generate a processor signal therefrom to control generation of the stimulation current; and a power source. One or more third nanowires may be disposed in close proximity to the one or more second nanowires, where the one or more third nanowires are adapted to detect a localized response to the stimulation current and provide feedback to the processor, which may be programmed to execute an algorithm for receiving the feedback and adjusting the stimulation current based on the localized response. Where the device is an retinal implant, the algorithm is based on a model for predicting retinal ganglion cell responses.

The one or more first nanowires may be a first nanowire array, where the first set of characteristics of the first nanowire array is selected for peak responsivity within a first wavelength range. The one or more first nanowires may further include a second nanowire array, wherein the first set of characteristics of the second nanowire array is selected for peak responsivity within a second wavelength range. The one or more first nanowires may also include a third nanowire array, where the first set of characteristics of the third nanowire array is selected for peak responsivity within a third wavelength range. The first set of characteristics may be selected to produce the first plurality of charges with a first quantum efficiency and the one or more second sets of characteristics are adapted to produce a second plurality of charges with one or more second quantum efficiencies.

The one or more first nanowires may be a power array adapted to act as the power source. The power array can be fabricated on a substrate comprising one or more p-n- junctions, wherein each p-n junction comprises a voltage drop adapted to accumulate charges for operation of the device. A separate substrate may also be provide having one or more separate p-n junctions in electrical communication with the power array wherein each separate p-n junction comprises a voltage drop adapted to accumulate charges for operation of the device. The surface of the separate substrate may be adapted to collect energy from an external energy source and generate charges therefrom.

The nanoscale dimensions of the inventive device allows multiple nanowire arrays to be combined, providing a device that combines one or more of the individual features and functions described above. For example, multiple nanowire arrays may be provided for a device that is capable of multi-spectral detection, self-powering and self-regulation. Based on the disclosure herein, numerous combinations and physical arrangements for achieving the described functions will become apparent to those of skill in the art.

BRIEF DESCRIPTION OF THE DRAWINGS

FIGS. 2a and 2b show nanowire arrays formed using the nanoimprint lithography (NIL) process flow; FIG. 2c shows the outer segments of photoreceptor neurons in a rat retina; and FIGS. 2d and 2e show examples of primary conical neurons cultured on the nanowire arrays.

FIG. 11a shows a simplified LC tank circuit, FIG. 11b shows the stages of an analytical model of the circuit of FIG. 11a, and FIG. 11c shows an LC resonant tank circuit with a diode.

FIGS. 18a-18h show results of ex vivo testing of the inventive system using retinal tissue from a rat.

DETAILED DESCRIPTION

According to the present invention, an integrated nanowire array device may be used as a sensor, a stimulator or both, as well as in various combinations to perform different functions within an integrated device. The sensor may detect stimuli such as optical or photonic, electrical, chemical, thermal, acoustic, other forms of energy, or any combination thereof. The invention may be incorporated into an implantable device or system for simulating natural biological signals in a subject who, through disease, injury or another condition, has partially or completely lost the ability to generate or process such signals on their own. The device may also be incorporated into a biological, chemical or environmental sensor for in vivo or in vitro research, or may be used for any application which might benefit from a nanoscale sensor, stimulator or both.

The following description relates to an exemplary application of the inventive device, in which silicon nanowires may be used as different components of a retinal implant. When light impinges on the implant, a photocurrent that is proportional to the intensity of light is produced. This photocurrent may be used to stimulate the neurons typically stimulated by the rods and cones. Electric currents produced in vertically aligned optoelectronic nanowire arrays are spatially localized and confined to the area of illumination determined by the incident light hitting the array, down to an individual nanowire. This level of precision means that localized spatial patterns of illumination on the array can potentially provide appropriate spatial retinotopic graded electrical stimulation, determined by the patterns and intensities of light in the visual scene.

Figure 1A:
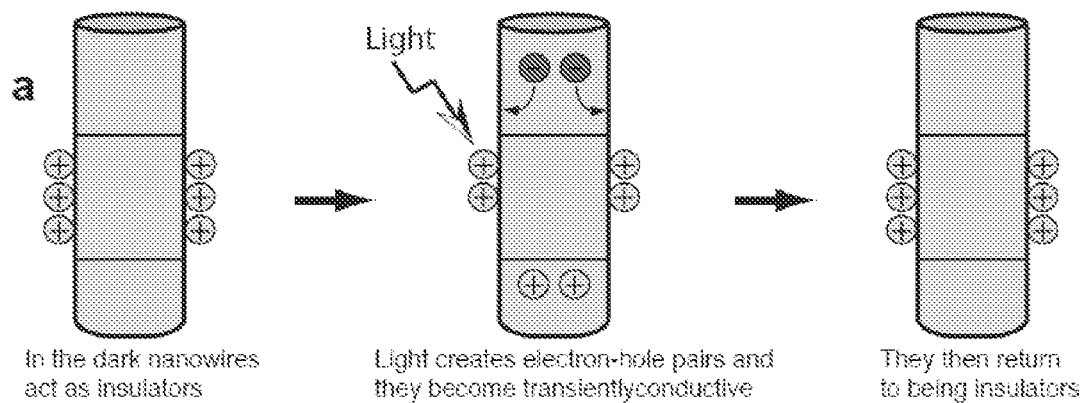
FIG. 1a is an energy band diagram of silicon nanowires in dark and light conditions.

Nanowires are capable of phototransduction and are well-documented as high sensitivity photodetectors. When visible light illuminates the nanowires, electron-hole pairs are generated. The electrons are instantly driven to the surface, leaving the holes in the center of nanowires. FIG. 1a provides an energy band diagram of silicon nanowires for the preferred embodiment of the nanowire structure ($p^+/p^-/p^+$). The holes in the $p^-$ region are depleted from the center and trapped in the surface states. The trapped charge at the surface creates a radial potential profile as shown. When a photon is absorbed by the nanowire to excite an electron-hole pair, the electron is instantly attracted to the surface and recombined with the trapped hole due to the radial potential, leaving the hole in the center of the nanowire to form a conductive channel. As soon as the nanowire becomes a conductive channel due to the presence of a hole that is free to move, current flows continuously from the anode to the cathode.

Figure 1B:
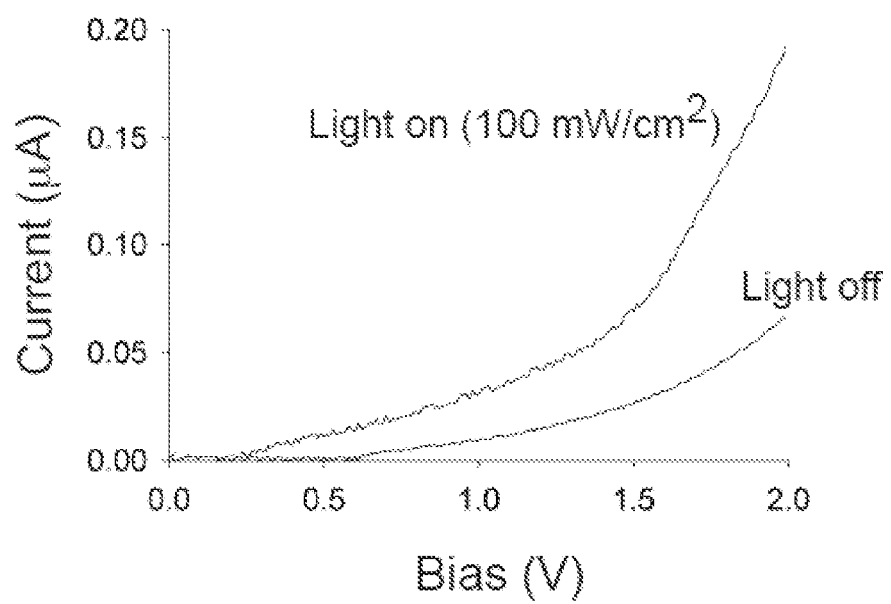
FIG. 1b is a plot of the I-V characteristics of silicon nanowire detectors.

Photoreceptors stimulate neural tissue via the release of neurotransmitters. Neurons can also be excited via current stimulation by driving a current through neural tissue. Artificially, depolarizing the cell membrane can be done by flowing ionic current between two electrodes. One of these two electrodes must be near the tissue. In the case of the present invention, the nanowires form the electrode. The photocurrent waveform can be altered via control circuits. Typically, the current waveform for neural stimulation is a monophasic, biphasic or triphasic current pulse. In an exemplary embodiment, the inventive nanowire devices can be biased to devices are specifically designed to produce biphasic voltage pulses that increase in amplitude in response to incident light. FIG. 1b is a plot of voltage output as a function of time. The amount of charge needed to stimulate the retina is around 1 µC (Coulomb), delivered over 5 msec, with a charge density of 1 mC/cm$^2$. Typical minimum waveform voltage amplitudes required to stimulate retinal ganglion cells are between 80-200 mV. Using the inventive device, this minimum can be achieved by a light stimulus on the order of hundreds of milliwatts/cm$^2$ at zero bias voltage, meaning that the nanowires were not driven by any external power and were able to actively stimulate ganglion cells in the retina strictly in response to the energy provided by the incident photons hitting the array. Current used for stimulation was 200 µA, with a maximum frequency of 100 Hz. Accordingly, the nanowires produce a photocurrent in response to light stimulation, which can be modulated by the applied bias.

Figure 2A:
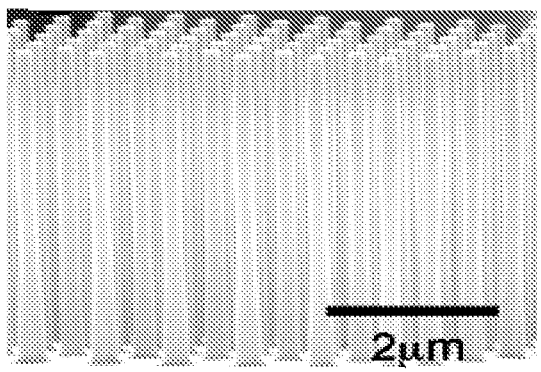
FIGS. 2a-2e are scanning electron micrographs (SEM's) of the optoelectronic nanowire arrays, where
Figure 2B:
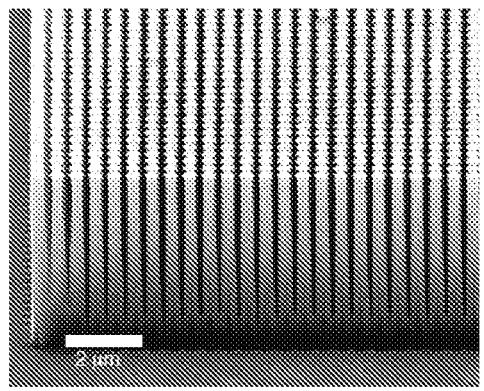

FIGS. 2a and 2b are scanning electron microscope (SEM) images of nanowires formed by the NIL process, which is described in International Publication No. WO2011/16326, as well as being described below. The packing density of the nanowires exceeds those of biological photoreceptors by over an order of magnitude, yet the nanowires can be fabricated to similar lengths. The lengths of human cone photoreceptors have been reported to be vary between 20 µm or less to about a maximum of 50 µm, depending on the type of cone, retinal eccentricity, and the particular individual subject studied. The cone diameters are between 1 to 1.2 µm. The mean density of human cones has been reported to be between 3,850 to 5480 per mm$^2$, with a peak density of between 147,300 to 324,100 at the foveal center. The relative size and density of human rod photoreceptors are roughly comparable but more uniform across the retina than cones. For example, their mean density ranges between 82,350 to 111,250 per mm$^2$, with peak densities between 161.000 to 189,000 per mm$^2$. By comparison, the inventive nanowires can be fabricated to be anywhere between 1 to 50 µm in length and between 0.2 to 5 µm in diameter, with a maximum packing density of about 25 million per mm$^2$. A summary of the comparative numbers is provided in Table 1.

TABLE 1

| Description | Length (µm) | Average Density (per mm$^2$) | Peak density (per mm$^2$) |
|---|---|---|---|
| Human cones | 20-50 | 3,850 to 5,480 | 147,300 to 324,100 |
| Human rods | 25-40 | 82,350 to 111,250 | 161,000 to 189,000 |
| Nanowires | 1-50 | 25 million (maximum) | |

Figure 2C:
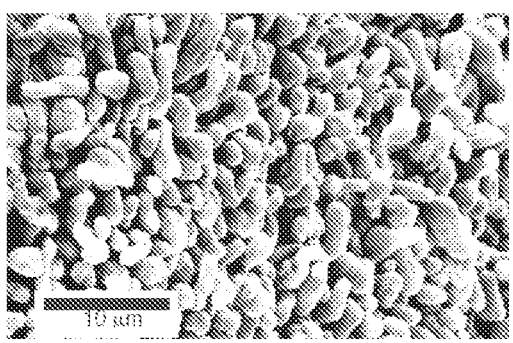

To provide a visual comparison. FIG. 2c shows the outer segments of photoreceptor neurons in a rat retina.

Nanotopography has been shown to improve tissue integration of prosthetic devices and even accelerate recovery from injury. The nanowire platform according to the present invention has an inherent nanotopography that facilitates interface directly with the ganglion cells. Recent work has shown that using nanotopography at the site of stimulation reduces the amount of current required to stimulate neural tissue, thus allowing power consumption to be minimized while simultaneously reducing the occurrence of tissue damage caused by the stimulation.

Figure 2D:
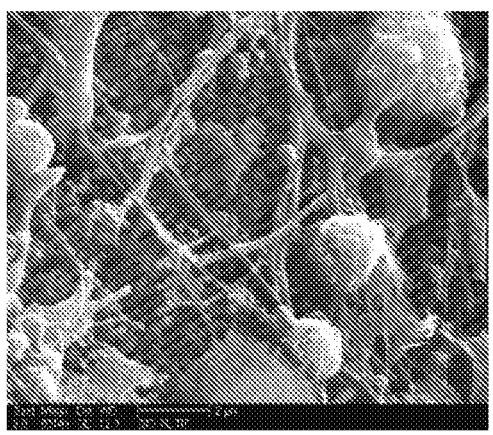
Figure 2E:
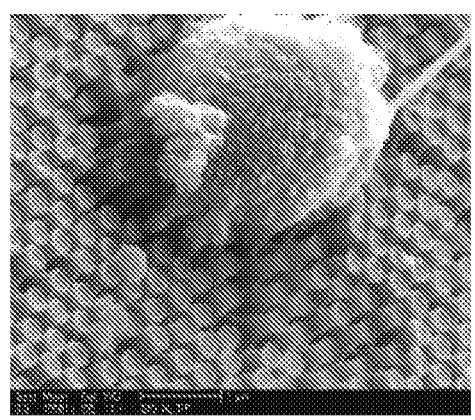

The inventive nanowire platform enables creation of an interface that is effectively a direct material-cell membrane biophysical interaction. FIGS. 2d and 2e provide examples of primary cortical neurons cultured on the nanowire arrays in vitro. There is extensive neurite outgrowth on the nanowires, and cultures remained healthy for up to one month. The interface between the nanoarrays and neurons is fundamentally biophysically and molecularly unique, involving molecular interactions that result in greatly enhanced abilities to stimulate and record using minimal input energy, e.g., currents, when stimulating. This nanoscale interface also makes it possible to record with excellent signal-to-noise ratios, requiring minimal amplification due to the intimate molecular interface between the nanowires and the neuronal cell membrane. These advantages are a direct result of the nanoscale engineering of the device and material.

Figure 3A:
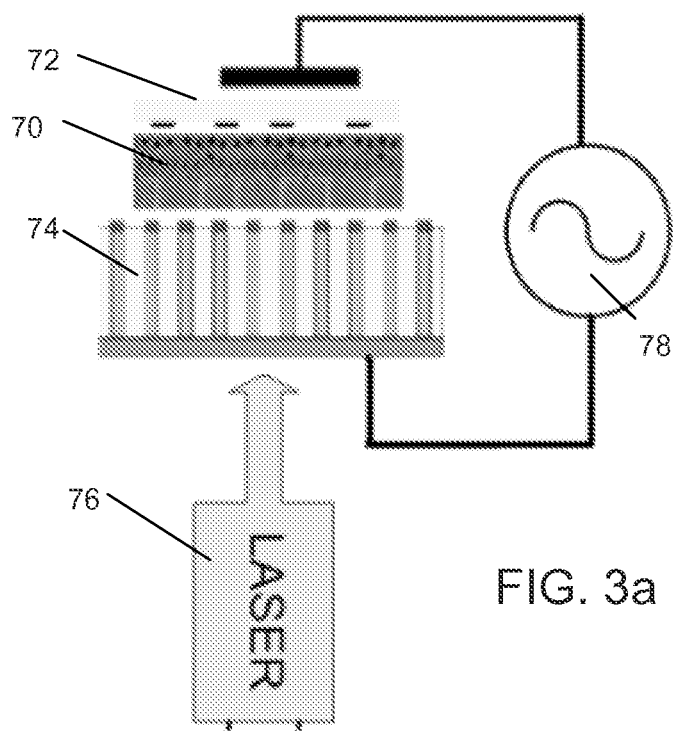
FIG. 3a is a diagrammatic view of an exemplary set-up for neurostimulation.

Nanowires can be used to produce a photocurrent to stimulate neurons to fire action potential in both monopolar and bipolar stimulation setups. If done in the retina, the stimulation will lead to visual percepts whether the stimulation is at the epiretina or subretina side. FIG. 3a illustrates an exemplary set-up for neurostimulation, where the retina 70 is placed in contact with a transparent (microelectrode array) 72 to record RG (retinographic) activity. The photocurrent produced by the nanowire array 74 in response to illumination by a light source (laser 76) can be used to inject current into the retina when placed near the tissue.

Figure 3B:
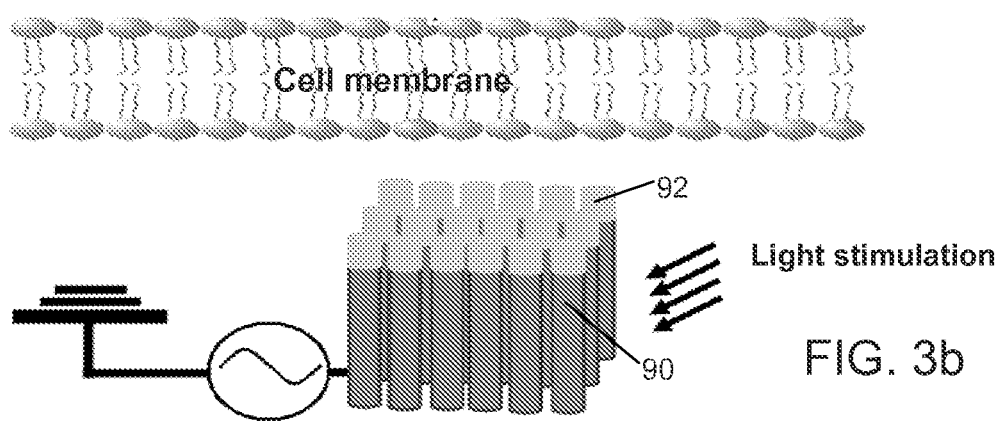
FIG. 3b is an exemplary embodiment of a stimulation set-up using the inventive nanowire platform.
Figure 3C:
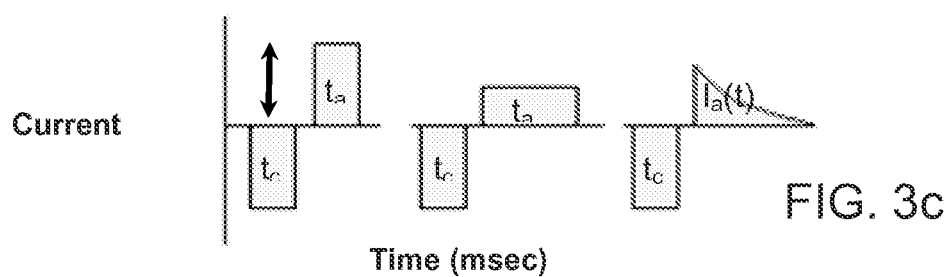
FIG. 3c shows the proposed current waveforms used to stimulate the array.

FIG. 3b is a diagram of an exemplary embodiment of an extracellular stimulation arrangement using the inventive nanowire platform with Si nanowires 90 and conductive metal (or metal oxide) 92. The number of nanowires per/bundle is dependent on the current output of the nanowires and will range from 1 nanowire to 1000 nanowires. FIG. 3c provides an example of current waveforms that can be used to stimulate $t_a$ and $t_c$, which range between 0.1 msec to 10 msec.

In addition to extracellular set-ups, the inventive nanowire platform can be applied to applications of intracellular stimulation. Excitable cells such neurons and heart cells can be depolarized by the extracellular or intracellular flow of ionic current. For intracellular stimulation, the nanowires can be engulfed inside the cell.

The silicon (Si) nanowire arrays used in the inventive devices may be formed using a nanoimprint lithography (NIL) technique, which is described in Kim, H., et al., "Fabrication of Vertical Silicon Nanowire Photodetector Arrays using Nanoimprint Lithography", *Proceedings of SPIE*, 2010, pp. 7591-7595, which is incorporated herein by reference.

The following is a description of an exemplary process for fabrication of nanowires for use in the integrated nanowire array devices.

Figure 7A:
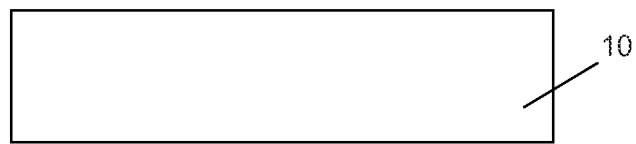
FIGS. 7a-7f diagrammatically illustrate the key steps in an exemplary process flow for fabricating vertical Si nanowires using the NIL process.
Figure 7B:
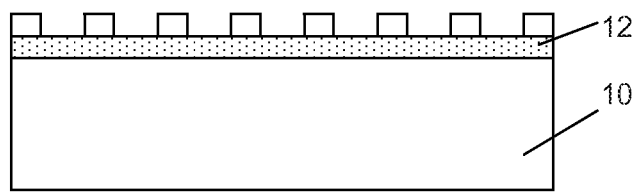
Figure 7C:
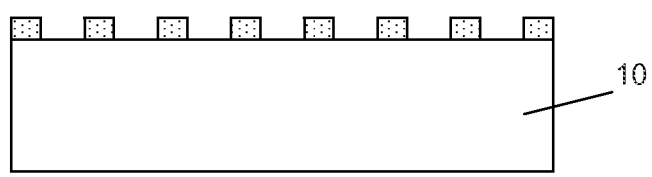
Figure 7D:
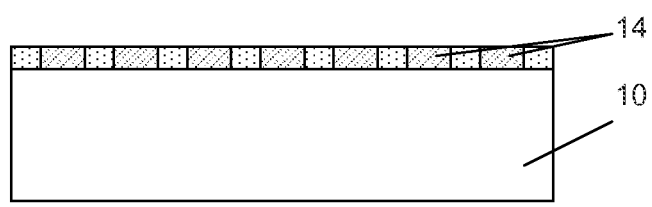
Figure 7E:
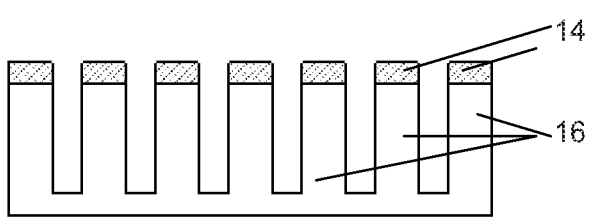
Figure 7F:
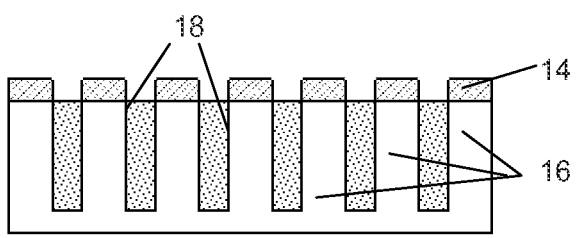

Nanoimprint lithography (NIL) involves physically pressing a mold, which has a nano-sized pattern, onto a photoresist-coated substrate. Generally, the NIL process consists of three steps: preparing a master mold, making a quartz working mold, and preparing the sample. Referring to FIGS. 7a-7f, the process for fabricating vertical silicon nanowires starts with a p$^+$ silicon <100> substrate with a lightly p-doped epitaxial layer covered by a heavily p-doped layer to form a p$^+$/p$^-$/p$^+$ epi structure (FIG. 7a). Photoresist is coated onto the epi structure 10 and is imprinted by pressing a surfactant-coated quartz working mold into the photoresist 12 (FIG. 7b) to create nano-islands of photoresist and expose the Si surface in the imprinted areas. Preferably, the photoresist has a two-layer structure with an under-layer and a UV-layer. The imprinted photoresist is cured using standard procedures according to manufacturer's specifications, followed by a reactive ion etch (RIE) process (two step RIE process if the preferred bi-layer PR is used) to expose the silicon surface in the imprinted areas (FIG. 7c). A ~70-80 nm layer of nickel 14 is deposited by evaporation and the photoresist nano-islands are lifted off to form an etch mask and to make ohmic contact with the upper p$^+$ region (FIG. 7d). This forms an array of Ni dots 14 on the Si surface. RIE is used to etch the exposed Si between the Ni dots, defining the nanowires 16 in the epi silicon (FIG. 7e), followed by annealing the Ni for hour at 650° C. The area between the nanowires 16 is filled with an insulating material 18 by spin coating the surface, baking for 5 minutes at 80° C., and using RIE to etch back the coating to expose the Ni tips (FIG. 7f). In some applications, it may be desirable to etch the coating back an additional amount to expose anywhere from 0.1%-50% of the lengths of the nanowires. In an exemplary embodiment, the insulating material 18 is polydimethylsiloxane (PDMS), but other materials known in the art may be used, including PARYLENE™ (poly(p-xylylene) polymers (all types, such as HT and C)), polyimide (all types), and poly(methylglutarimide (PMGI)).

The key to the inventive nanowire platform for implants is the ability to precisely control dimensions and spatial distribution on a nanoscale. This level of precision may be achieved through top-down or bottom-up formation of the nanowire arrays.

In one embodiment of the invention, the nanowires can be fabricated on a substrate such as PARYLENE™, instead of Si, to take advantage of its superior biocompatibility and long term stability. PDMS (polydimethylsiloxane), which has similar properties, may also be used as a substrate. PDMS is an optically transparent, non-toxic elastomer with high permeability to allow provision of nutrients to the tissue in which the device may be implanted. Other polymers with similar properties may be also be used. Selection of appropriate materials will be readily apparent to those of skill in the art.

An important step in the fabrication of nanowires is formation of the contact electrodes to each nanowire. This electrode (typically consisting of Ti/Au, although other metals may be used) should connect all nanowires, which are about 1 μm apart, without blocking channels for nutrients needed to maintain the health of the retina. FIGS. 8a-8e illustrate an exemplary process flow for removing the nanoimprinted silicon nanowire arrays from its native silicon substrate to a flexible substrate formed from a polymer such as PDMS, PARYLENE™ or other materials with similar properties.

Figure 8A:
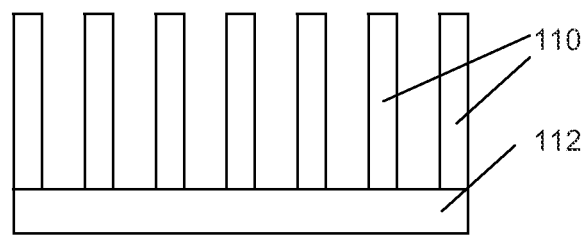
FIGS. 8a-8e diagrammatically illustrate the key steps in an exemplary process flow for forming a nanowire artificial photoreceptor according to the present invention.
Figure 8B:
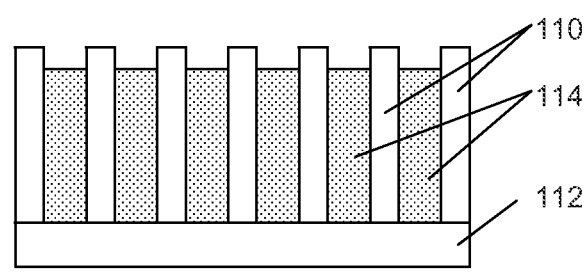
Figure 8C:
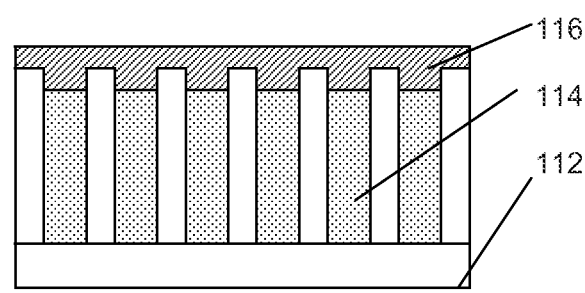
Figure 8D:
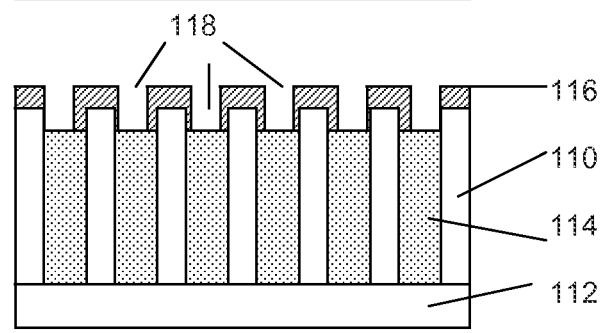
Figure 8E:
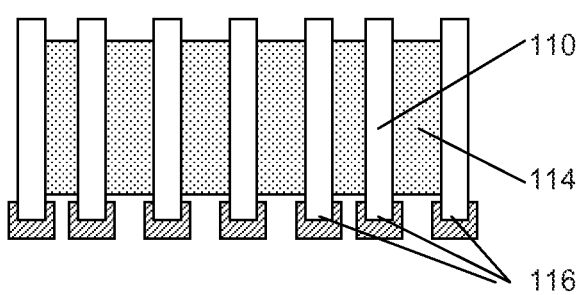

After formation of nanoimprinted Si nanowires 110 on an SOI (silicon-on-insulator) wafer 112 (FIG. 8a), a layer of PDMS membrane 114 is spin-coated onto the substrate (FIG. 8b). After partial removal of the layer to expose the tips of nanowires, a layer of Ti/Au 116 is deposited to form contacts with the nanowires (FIG. 8c). UV lithography is performed to open up holes 118 in the spaces between the nanowires (FIG. 8d) to provide nutrient supply channels to the retina. The exact size and position of these holes on the Ti/Au metal layer is not critical, as long as they are located in the spaces between the wires. The final step (FIG. 8e) is to release the wires from the SOI substrate 112 by removing the buried oxide layer. (The nanowire array is shown inverted in FIG. 8e.) The released structure can be placed onto a PDMS handle wafer to facilitate handling and material transfer.

Figure 4A:
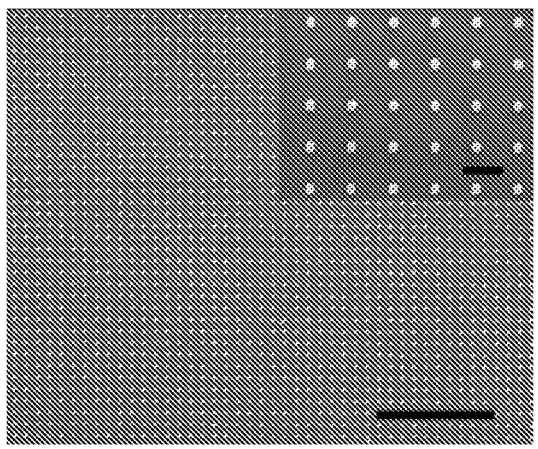
FIGS. 4a and 4b are top and side perspective view SEM images, respectively, of multiple nanowire arrays fabricated on a single substrate.
Figure 4B:
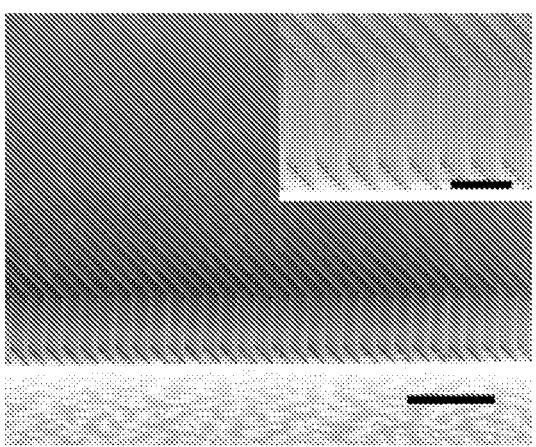

The use of nanoimprinting to manufacture the nanowire array provides control over spacing between the nanowires down to 2 nm, diameters ranging between 10 nm-5 μm, and lengths ranging between 1-50 μm. This level of control allows the nanowires to be tailored to fit the distribution of the PRs they are replacing, if appropriate. Virtually any distribution pattern can be formed using the NIL process, adapted for the requirements of the particular application. FIGS. 4a and 4b, which are SEM images of a nanowire array, provide one example of a nanowire arrangement where arrays of nanowires of two different diameters, densities and lengths are integrated onto a substrate. (The bars in the image represent 1 μm.) These properties make the nanowires an excellent candidate for replacement for the photoreceptors.

Figure 6A:
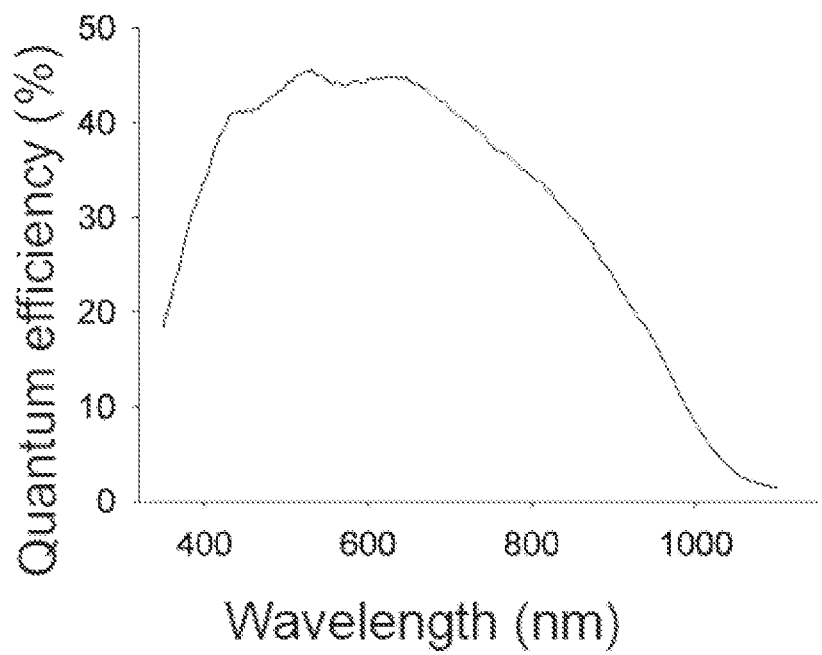
FIGS. 6a and 6b are plots of quantum efficiency versus wavelength for nanowires covering the entire response range and for nanowires optimized for specific sub-ranges within the entire response range.

Quantum efficiency is the ratio of the fraction of photons hitting a photoreactive surface that result in an electron-hole pair, which in turn transiently produce a flow of currents through the nanowires as a function of their nanotopography and doping levels. The current-voltage characteristics of the nanowires are shown in FIG. 1b. In tests of nanowires fabricated using the above-described process, the nanowires were biased from −2 to 2 V in Ringer's solution (an isotonic solution relative to the extracellular environment) and the current measured in a 1 M-ohm resistor. Nanowires created using the above-described NIL process display high quantum efficiency, with an electron-hole pair being generated by close to every two photons, i.e., ~50% quantum efficiency, on average, over a broad range of wavelengths. This efficiency is comparable to that of high-end CCD cameras. FIG. 6a is a plot of the quantum efficiency as a function of wavelength for the nanowires having dimensions selected to cover the entire range of around 350 nm to 1100 nm. The peak quantum efficiencies approach 50% toward the longer visible light range, tailing off toward the higher end of the range.

Figure 6B:
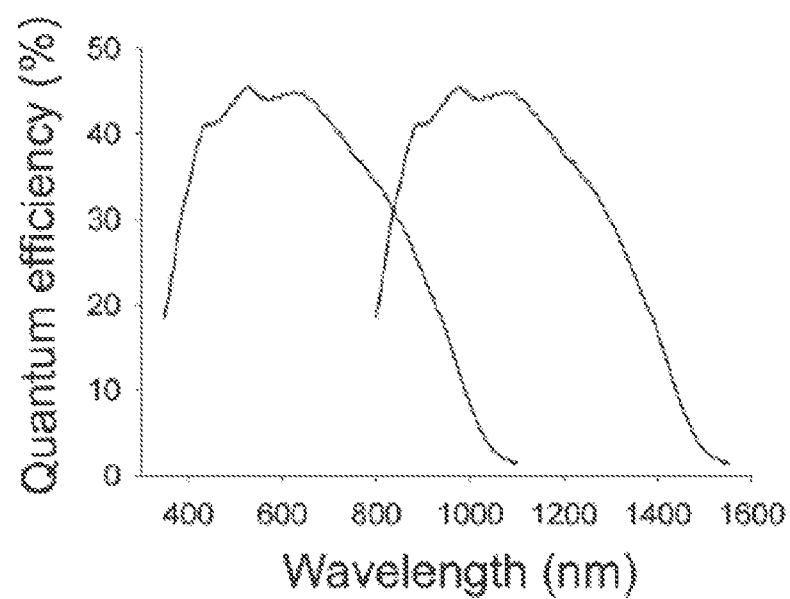

The nanowire arrays may be fabricated to include nanowires of two or more different dimensions, i.e., diameters and/or lengths, to provide the ability to detect optical signals within different wavelength ranges. Devices fabricated with silicon nanowires according to the NIL processes described above respond from about 350 nm to about 1100 nm (with ~50% peak quantum efficiency), exceeding the normal range of human vision, which covers a range of around 400 nm to 700 nm. Using the NIL process, the nanowires may be combined in virtually any combination of diameter, length, pitch, density or pattern, either by fabrication on a single substrate or fabrication on separate substrates which can then be combined when the different arrays are attached to a flexible substrate. FIG. 6b is a plot of quantum efficiency for two nanowire arrays in which each array has been optimized through selection of dimensions during fabrication for sensitivity across two different, partially overlapping spectral ranges—350 nm to 1100 nm and 800 nm to 1580 nm. Thus, by selection of the nanowire dimensions, the wavelength range(s) and the peak quantum efficiency may be optimized for the desired application.

Figure 5A:
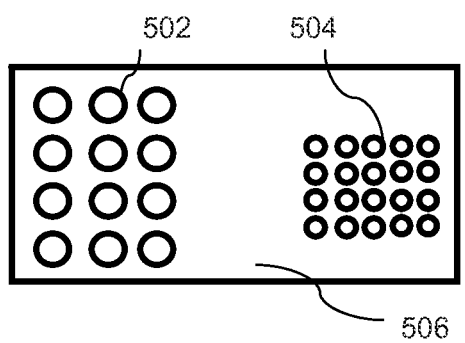
FIGS. 5a-5c are diagrammatic top views of exemplary combinations of nanowires with different physical and performance characteristics.
Figure 5B:
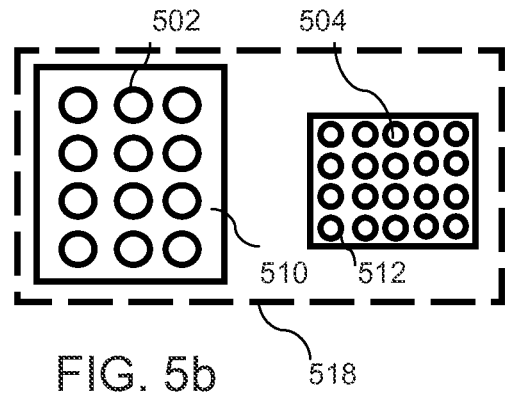
Figure 5C:
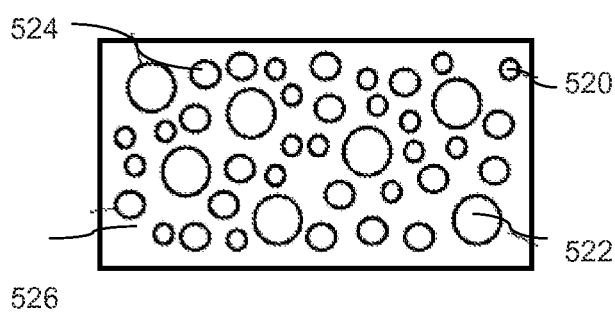

FIGS. 5a-5c illustrate a variety of possible permutations that may be used to construct an integrated device capable of detecting different wavelengths or wavelength ranges, and or optimized for performing different functions, such as power generation, as described below. FIGS. 5a and 5b are top views of a combination of different diameter nanowires which may be selected to detect two different wavelength ranges. In FIG. 5a, the arrays 502 and 504 for detecting different wavelengths may be fabricated on the same substrate 506, while in FIG. 5b, the arrays 502 and 504 may be fabricated on separate substrates 510 and 512, which may then be affixed to a flexible substrate 518 and connected to the device processor (not shown) using appropriate interconnection means. This approach can be used to permit one array to "float" relative to the other, which may facilitate optimization of the relative locations of the arrays based upon the wavelengths to be detected. The nanowires in arrays 502 and 504 may have different diameters (as illustrated), or they may have different lengths, densities, quantities or pitches to optimize the desired response. FIG. 5c illustrates another exemplary combination that may be used for three different diameter nanowires 520, 522 and 524, which are shown fabricated on a single substrate 526 with the three different diameter nanowires spatially integrated into a single array. The illustrated example includes a larger quantity of small diameter nanowires 520, with relatively fewer large diameter nanowires 522. Such combinations may be made to enhance spectral responsivity, quantum efficiency, current levels or other characteristics of the device as needed for the desired application. Alternatively, the three different diameter nanowires may be segregated, similar to the examples shown in FIGS. 5a and 5b. To further extend the example, three distinct nanowire diameters may be used to simulate the three types of human cones—L (long (564-580 nm peak)—red), M (medium (534-545 nm peak)—green) and S (short (420-440 nm peak)—blue)—to provide the basis for a retinal prosthesis that enables high-resolution color vision. Other combinations of spectral responsivity may be used depending on the application. For example, infrared or ultraviolet ranges may be included.

The integrated nanowire array devices may include the ability to self-regulate by providing an additional phototransduction nanowire array. The additional array may be used to detect cell responses to stimulation to allow measurement of the cells' receptive field, the data from which may be used to determine appropriate parameters for stimulating ganglion cells in the vicinity of the stimulus. The device processor may include programming to implement algorithms for processing the measured response information from, and ultimately stimulate, nearby cells. In a retinal implant, the response signals from the ganglion cells may be processed in the device processor using an algorithm based on a model of ganglion cell circuitry. Models for predicting retinal ganglion cell responses, including the linear-nonlinear Poisson (LNP) model, integrate-and-fire (IF) model, and the generalized linear model (GLM), are known in the art. In an exemplary embodiment, a GLM is used, in which light information is integrated over time and space according to an average receptive field profile that includes chromatic information. The signal is passed through an exponential nonlinearity to mimic spike generation nonlinearity, and spikes may then be generated stochastically. Associated with every spike, a characteristic waveform is fed back into the linear stage to implement temporal structure in the spike train. As with the feedback signal, every spike produces a characteristic waveform fed into the linear stage of other cells of the same type, producing correlated activity that closely simulates what is observed in the retina. Given that the GLM is as accurate a model as any in the field, is fitted to primate data, and is very simple in structure, it is a good candidate for forming the basis of the signal processing circuitry that drives spikes in a prosthetic device. By applying the algorithm, the inventive device is able to stimulate the cells in a manner that approximates the natural visual signals that are normally transmitted to the brain. As will be readily apparent to those in the art, other models may be implemented, or a variety of different models may be programmed within the processor, leaving selection of the appropriate model for a given patient up to the researcher or clinician at the time the implant is placed. Also included within the processor may be one or more machine learning algorithms that allow the device itself to learn the best model for the specific conditions, for example, to make adaptations to compensate for disease progression.

An integrated nanowire may be used as a low power sensor. The nanowires as described herein may use multiple leads or a single lead. Only a single lead may be required to bias an array as large as 15×15 mm, for example, which would have a 2 KΩ impedance equivalent to a 0.04 μW power consumption for the entire array. A 15×15 mm array would have about 375 million nanowires, each representing a potential individual stimulation site. The power consumption could also be calculated as a density of nanowires per array and may scale with the size of the device. For a device with a size of 15 mm$^2$, the power consumption may be between 1 μW to 0.1 μW. For a retinal implant, the device may be as large as 1200 mm$^2$ for a retinal device, with the power consumption scaling up accordingly.

Figure 9A:
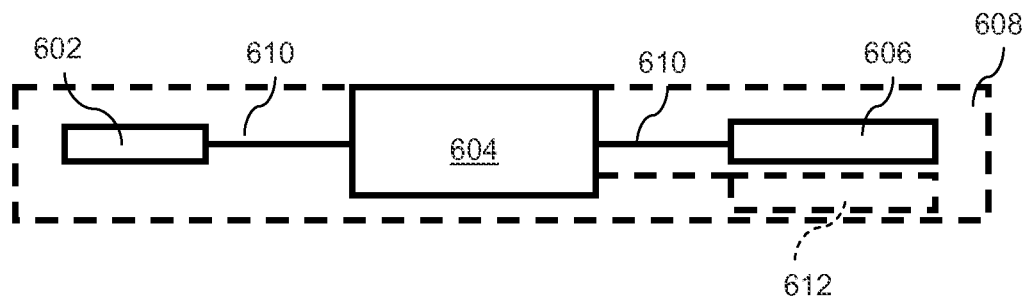
FIGS. 9a-9c are diagrammatic views of different embodiments of a self-regulating device according to the present invention.
Figure 9B:
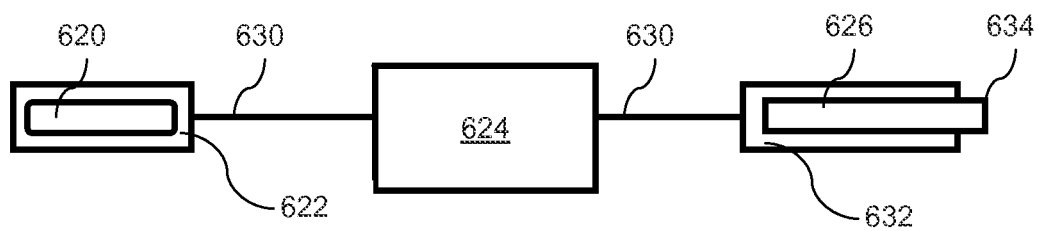
Figure 9C:
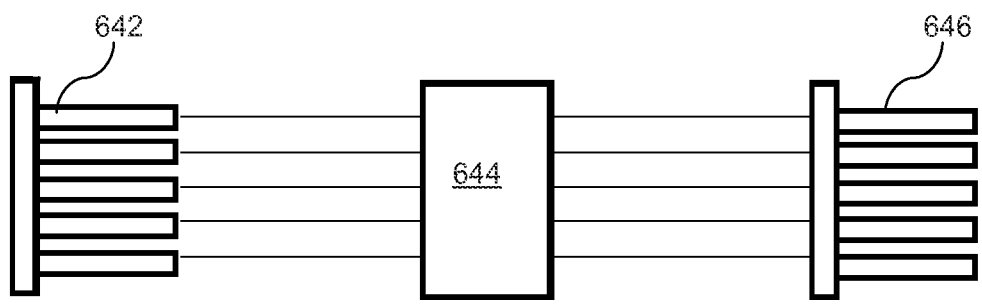

The self-regulating embodiment of the nanowire array device may be implemented using a number of different configurations, a few examples of which are diagrammatically illustrated in FIGS. 9a-9c.

FIG. 9a illustrates a first exemplary configuration, which includes a nanowire sensor 602, an integrated circuit (IC) 604 including a processor, and a stimulator 606, which are in electrical communication via interconnect 610. The processor is programmed to sample signals produced by the sensor 602 and compute the correct electrical stimulation for each ganglion cell with a receptive field that covers the stimulation space. The stimulator 606 may then provide electrical stimulation of the ganglion cells based on the computations of the algorithms to the incident light. In one variation, an additional nanowire sensor 612 (shown with dashed lines) may record local ganglion cell responses in close proximity to the location of the stimulation to allow further processing by algorithms in the processor. The processing circuitry may then optimize and fine tune the electrical stimulation output to the ganglion cells. The stimulator 606 may be a microelectrode, nanowire, or carbon nanotube. All basic components (602, 604 and 606) may be fabricated on the same substrate, fabricated on separate substrates that are then affixed to a flexible substrate 608, or they may be separate substrates that are linked by a flexible interconnect to facilitate optimal placement of the sensor 602 and or stimulator 606 for the desired performance. It should be noted that the configuration of nanowire sensor 602, as well as the quantity of nanowires in the sensor, will be determined by the desired application and performance. Thus, while a single nanowire is illustrated in the example, more nanowires may be included in the sensor as well as the stimulator, an example of which as shown in FIG. 9c. The nanowires of sensor 642 are connected to IC 644, which is connected to the nanowires of stimulator 646. Multiple nanowire arrays may be used for the sensor, the stimulator or both. Further, an additional sensor (single or multiple nanowires) and one or more stimulator arrays may be in close proximity to each other (e.g., sensor 612 in FIG. 9*a*) to provide highly localized measurement for precise control of device operation.

FIG. 9*b* illustrates a second exemplary configuration of the self-regulating device, which includes a floating nanowire 620, which may be embedded within a flexible substrate 622 and/or coated with an insulating material, which may serve to isolate the nanowire from adjacent nanowires. The floating nanowire 620 may be in electrical communication via interconnect 630 with integrated circuit 624 which is also connected to a stimulator 626. The stimulator 626 may be at least partially coated with an insulating material 632 or embedded in a flexible array with a conductive tip 634 extending through the insulating material to deliver the appropriate current for stimulation. A variation on the configuration of FIG. 9*b* may include two or more separate nanowires 620, each connected to IC 624 and two or more separate stimulators 626, connected to IC 624 for delivering stimulating current based on signals from the processor in IC 624. The multiple stimulators may be in the form of separate arrays, or they may be spatially integrated, with the different stimulators distributed throughout a single array. Where multiple nanowires 620 are used, a first may function as a detector while one or more second nanowires may perform the function of a power source, as described below. Additionally, multiple control ICs 624 may be used, with a dedicated IC for each sensor/stimulator combination. The multiple sensors, ICs, and/or stimulators may be combined on the same substrate, on separate substrates, or any combination thereof.

Figure 10B:
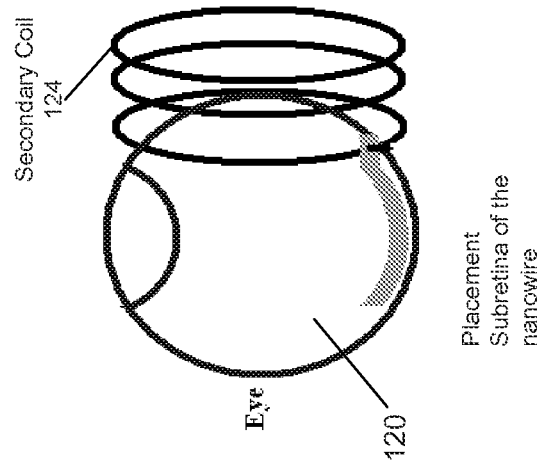
FIGS. 10a and 10b are diagrammatic views of one embodiment for powering a nanowire-based retinal implant.
Figure 10A:
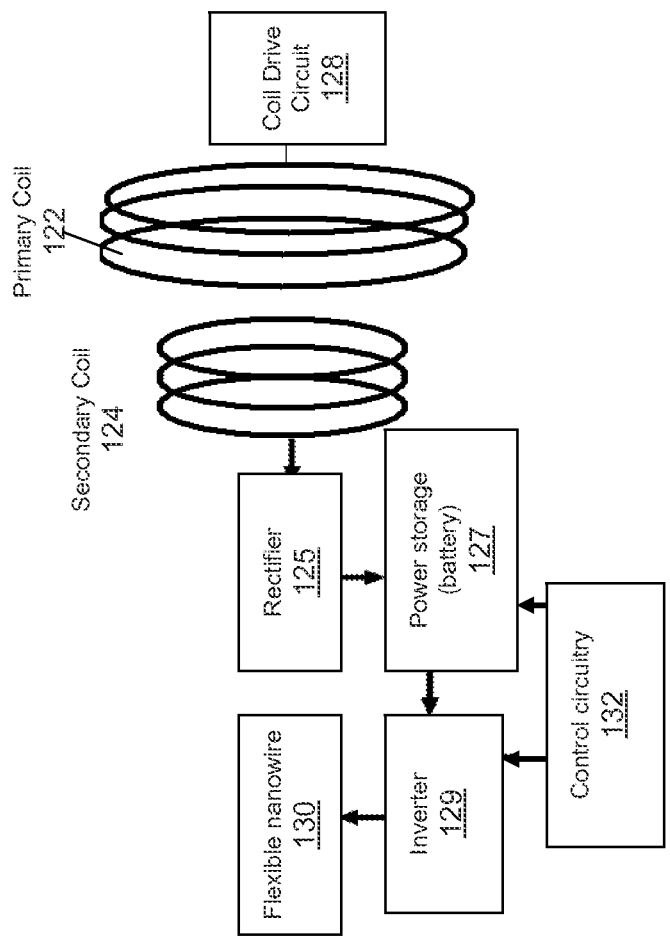

A number of different structures and methods may be used to provide power for operation of the integrated nanowire device. One approach for powering the prosthetic devices uses coupled coil transmission—this approach has been adopted by groups involved in the retinal prosthetics. Referring to FIG. 10*a*, the coil transmission assembly can include an AC magnetic field generated by a primary coil 122 on the outside of the eye 120, mounted, along with a coil drive circuit 128, on a pair of glasses that can be worn by the patient. Placement of the secondary coil 124 can be at the temporal side of the eye 120, as shown in FIG. 10*b*, to simplify transmission. This allows the coil and electronics to be attached to the sclera on the outside of the eye, while the electrodes of the nanowire array extend through a flap in the sclera to the subretinal space. Alternatively, the coil 124 could be placed against the retina, which would be most convenient since the coil, electronics and nanowire array could be implanted as one package. However, the fragility of the retina precludes placement of a thick or heavy implant, thus limiting the possible power that could be delivered. Placing the coil in the anterior chamber would allow more power to be delivered but is surgically difficult. Another alternative is to place the coil on the outside surface of the eye under the conjunctiva on the front of the eye. This location, or the location on the temporal side of the eye, allows the greatest amount of power to be delivered.

The design of secondary coil 124 will be limited by the maximum space around the eye and the heating due to the magnetic field (ANSI limit for field induced power in a tissue is 178 μW). The wireless circuit shown in FIG. 10*a* includes a rectifier 125 to convert the AC field induced by the primary coil 122 to DC for storage by battery 127. This is a typical design for inductive power delivery. However, because the nanowires 130 require AC bias to produce the biphasic currents needed for neural stimulation, an inverter 129 may be included to convert the DC back to AC. Control circuitry 132 is connected to battery 127 and inverter 129 for controlling operation of the nanowire array 130. This design, although expected to be robust, may consume excessive of power for practical implementation.

In some applications for neurostimulation, the rectifier and inverter may be eliminated, and the AC induced field could be used to directly power the nanowires. Because this approach is frequency limited, it may be more appropriate for neurostimulation applications other than retinal stimulation. In this embodiment, it may be advantageous to change the site or size of secondary coil to improve alignment with the primary coil. In other embodiments, the device may simply be powered by a small battery such as those used in hearing aids.

Figure 11A:
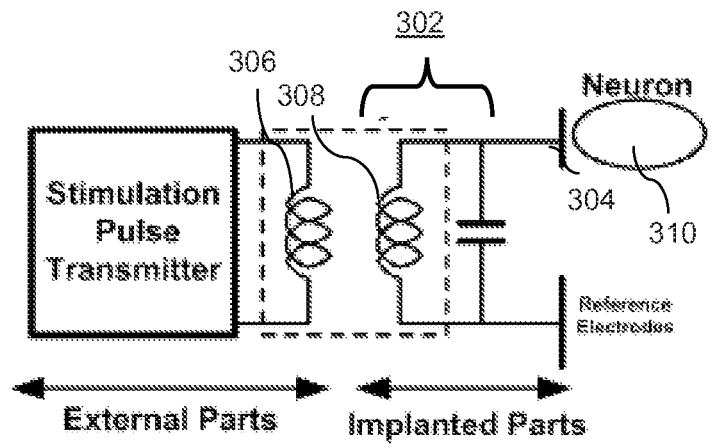
FIGS. 11a-11c are diagrammatic views of a second embodiment for powering a neural stimulator using an LC resonant tank circuit, where
Figure 11B:
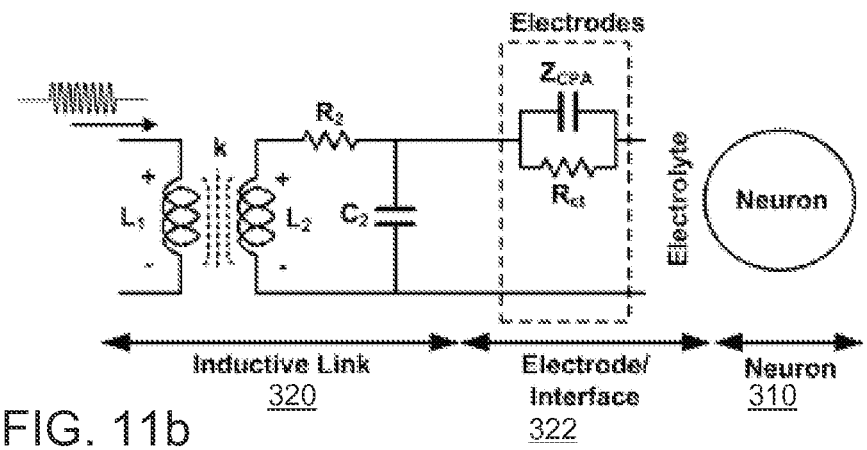

As another option for powering an implanted device, the present invention may employ a stimulation circuit that wirelessly produces a current appropriate for neural stimulation. FIG. 11*a* illustrates a simplified architecture for wireless neural stimulation with only an LC resonant tank 302. This circuit couples the electrode 304 directly to the inductor coil pair 306, 308, and uses the train of sine wave pulses that are received directly from the external primary coil inductor 306 to stimulate the neuron 310. Using this approach, the resonance frequency of the inductive link should be the same as the frequency of the stimulation pulses in the neural interface. However, the resonance frequency of the inductive link typically exceeds 1 MHz, while neurons require stimulation pulses in the kHz frequency range. The analytical model for the architecture can be divided into three stages: inductive link 320, electrode-neuron interface 322, and neuron 310, as illustrated in FIG. 11*b*.

In most biomedical applications, the primary inductor is placed externally and is less constrained than the secondary inductor, which must fit within the body, be flexible to facilitate contact to the tissue, and be insulated for biocompatibility. These constraints can be met using microfabrication.

A prototype stimulator was constructed by patterning a planar double-spiral coil onto a flexible substrate, which was folded for two-fold increased inductance in a simple polyimide-metal-polyimide fabrication process. A single metal layer can be used by locating electrodes and solder masks for electrical components in the center of the coil. The inductance $L_2$ and the quality factor $Q_2$ of the coil can be calculated according to the following equations:

$$L_2 = 2\frac{r^2 N^2}{20r + 28d} \quad (1)$$

$$Q_2 = \frac{\omega L_2}{R_2} = \frac{\omega\left(2\frac{r^2 N^2}{20r + 28d}\right)}{\rho\frac{2\pi r N}{wh}}, \quad (2)$$

where the coil parameters are: number of windings N, mean radius r, depth d, resistivity ρ, width w and height h of the metal line.

Using practical values for each parameter (6 cm for diameter of the coil and h=200 nm), $Q_2$ is less than 0.1 in 100 kHz. For a given geometry, the number of windings does not contribute to the quality factor of the coil. When either the resonance frequency is over 1.5 MHz or the height of the deposited gold layer is over 3 μm, the quality factor of the coil can be greater than one. Increasing the quality factor by increasing the size of the coil is not practically achievable.

Because subcellular spatial resolution is not required in this analysis, a point-contact model can be used to model the electrode-neuron interface. The membrane of the neuron is divided into two domains: a free membrane and an attached junction membrane, which is close to the electrode. The stimulation signal is transferred to the junction membrane and the free membrane is assumed to be connected to ground. For analysis of the electrode-neuron interface, each membrane domain can be modeled with passive elements. The transfer function $H(j\omega)=V_j(j\omega)/V_{STIM}(j\omega)$ for stimulation is:

$$H(j\omega) = \frac{Z_{neu} // R_{seal}}{R_{spread} + Z_{el} + Z_{neu} // R_{seal}} \frac{\frac{R_M + R_J}{1 + j\omega \frac{O_{mem}}{g_{mem}}}}{Z_{neu}} \quad (3)$$

$$Z_{neu}(j\omega) = \frac{R_M + R_J}{1 + j\omega \frac{O_{mem}}{g_{mem}}} + \frac{1}{j\omega C_{hd}} \quad (4)$$

$$Z_{el}(j\omega) = Z_{CPA} // R_{ct} \quad (5)$$

The electrode-neuron interface behaves as a bandpass filter with variation in cut-off frequency and amplitude of the transfer function as a function of diameter of the electrode and the gap between the electrode and the neuron. At 100 kHz stimulation frequency, at most 20% coupling efficiency can be achieved using practical values obtained from the literature.

Extracellular electrical stimulation decreases $V_j$, the voltage across the junction between the electrode and the neuron and depolarizes the membrane voltage activating sodium current flow into the cell. A train of biphasic stimuli of sub-threshold amplitude has been shown to depolarize the membrane by the repetitive activation of sodium channels. To study the repetitive sub-threshold stimulation, a two-domain model with two separate membrane domains can be used—an attached junction membrane and a free membrane. Both membranes are modeled after Hodgkin-Huxley (H-H), and for the junction membrane, the $Na^+$ channels are considered to have sustained voltage-dependent conductance. The limited dynamics due to the m and h variables in the H-H model does not allow effective stimulation higher than a few kHz. The faster dynamics of the sustained $Na^+$ conductance model suggests that 100 kHz stimulation may initiate an action potential by repetitive inward sodium current depolarizing membrane voltage. However, even if 100 kHz neural stimulation can be effective, it is still out of the practical range for high-Q inductive stimulation.

Figure 11C:
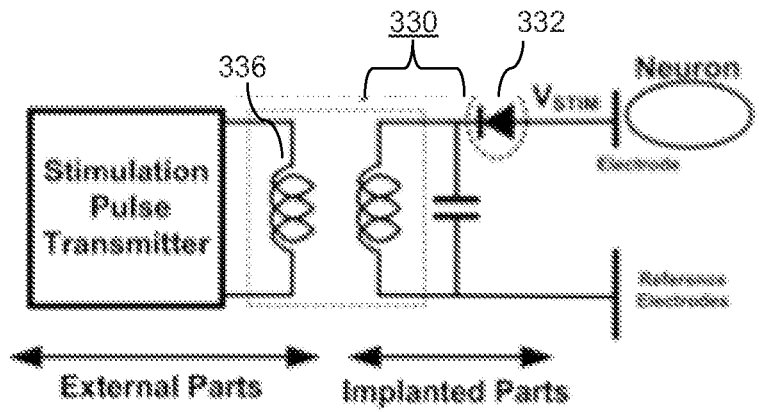
Figure 12:
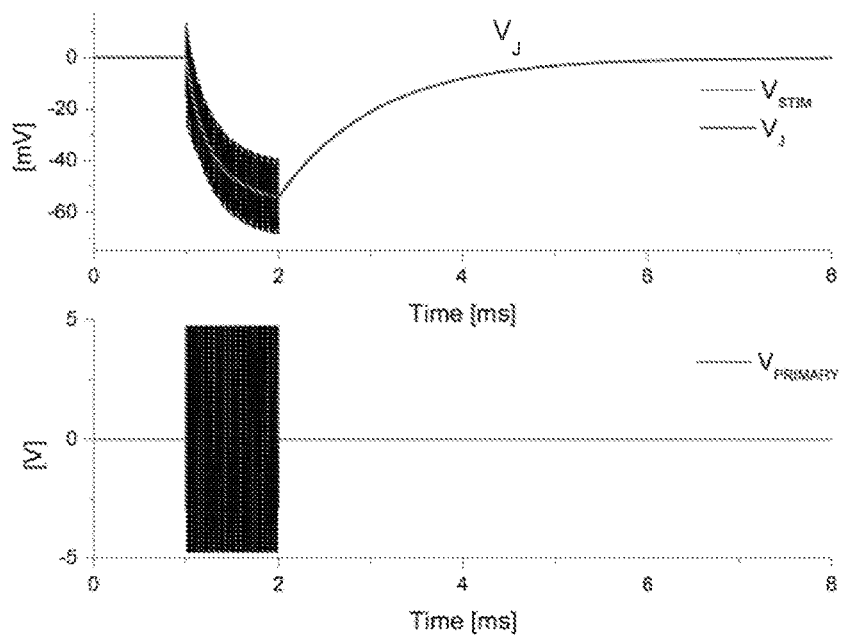
FIG. 12 illustrates neural stimulation using the LC resonant tank circuit and diode for powering the nanowire array device with a 1 ms, 10 MHz sine pulse from an external transmitter.
Figure 13A:
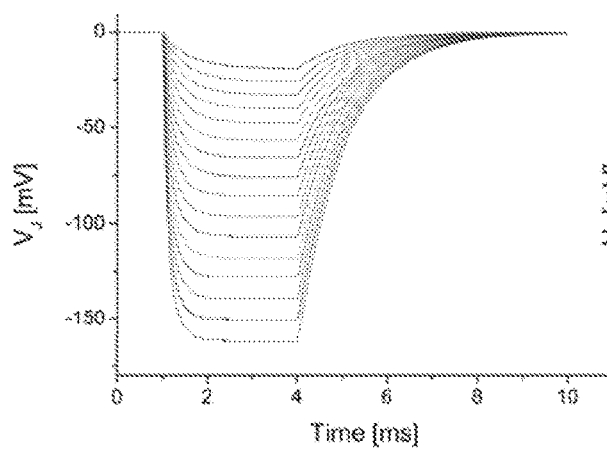
FIGS. 13a and 13b are plots showing how the strength and width of the pulse produced by the LC resonant tankidiode circuit are individually controlled by changing the amplitude (FIG. 13a) and number of pulses (FIG. 13b) of the primary input voltage.
Figure 13B:
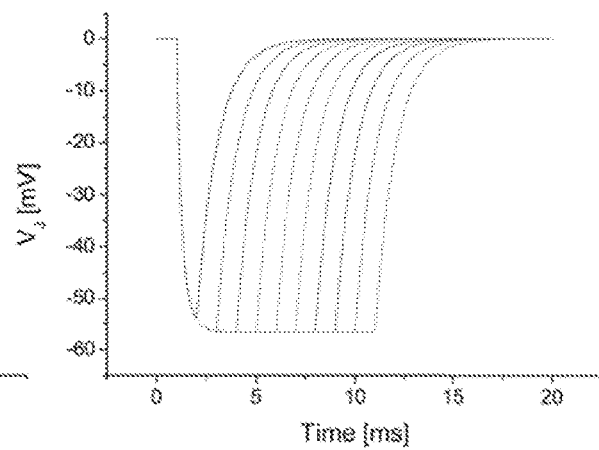

As established by the preceding analysis, direct inductive neural stimulation is not practically feasible. However, accounting for rectification and lowpass filtering between the secondary coil and membrane junction, it is possible to bridge the gap between the optimal frequency ranges for high-Q induction and neural stimulation. The stimulation circuit shown in FIG. 11c includes an LC resonant tank circuit 330 and a diode 332. The diode 332 serves to rectify the incoming sine wave to generate a monophasic pulse for neural stimulation. FIG. 12 illustrates neural stimulation with a 1 ms, 10 MHz sine pulse from the external transmitter (primary coil 336). The strength and width of the pulse on the junction are individually controlled by changing the amplitude (FIG. 13a) and number of pulses (FIG. 13b) of the primary input voltage in the external part.

A test device was constructed for testing on retinal tissue. Polyimide was spun on a silicon wafer to a thickness of 10 microns (Pyralin PI 2611 from HD Microsystems) and cured according to the manufacturer's specifications. E-beam evaporation was used to deposit 200 nm of gold with a 10 nm chrome adhesion layer. The coils were patterned by etching the gold and chrome after patterning with photoresist using conventional methods. Insulation was added by spinning on a polyimide layer of 5 μm.

Retinal tissue was obtained by excising the eyes of an adult rat that had been sacrificed. The eyes were placed in Ringers solution bubbled with 95% $O_2$/5% $CO_2$ at 30° C. The Ringers solution contained (in mmol/L): 117.0 NaCl, 3.0 KCl, 2.0 $CaCL_2$, 1.0 $MgSO_4$, 0.5 $NaH_2PO_4$, 15.0 D-glucose, 32 $NaHCO_3$, and 0.01 L-glutamate. The eye cup was perforated and cut around the ora serrata with a surgical scissor. The lens was removed and the retina loosened from the sclera with fine forceps, taking care not to touch the retina. The dissection was performed under a dissection microscope. The retina was then moved to a Microelectrode array (64 channel MEA, from Multichannel System (Germany)) by mounting on filter paper and then placed ganglion side down. The retina was left for 15 minutes in continuously perfused oxygenated Ringers solution. The retina was bleached prior to testing by exposure to a surgical light for 5 minutes.

Figure 14:
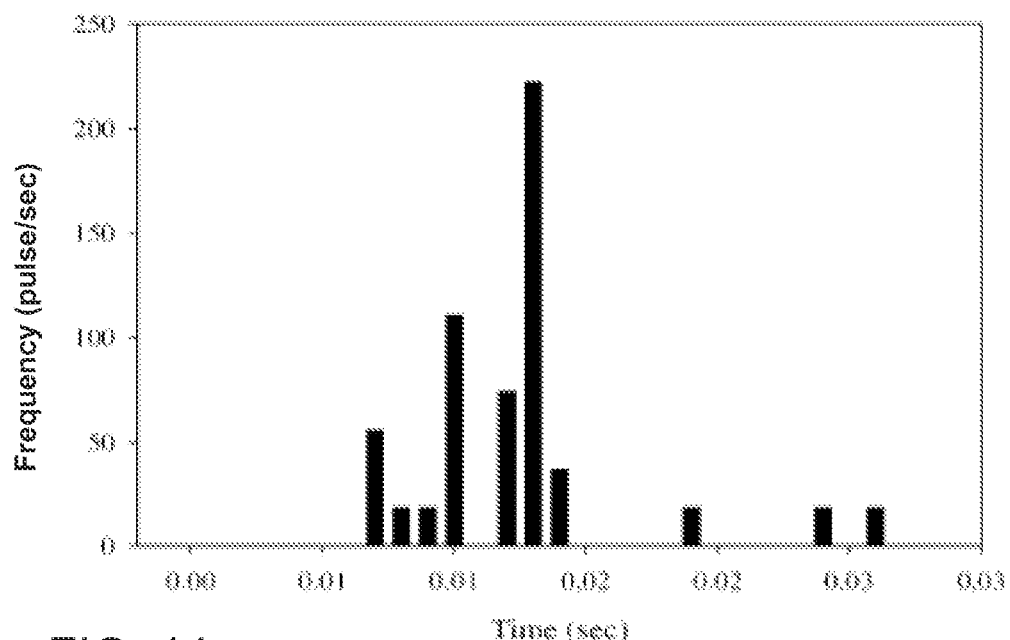
FIG. 14 is a peristimulus time histogram (PSTH) for six ganglion cells responding to six stimulation pulses using the embodiment of FIG. 11c.

The rectified generated pulses of FIGS. 10a and 10b were loaded through LABVIEW® design system software (National Instruments Corporation, Austin, Tex.) and the analog output was used to stimulate the retina via one of the MEA channels. The results in FIG. 14 show the peristimulus time histogram (PSTH) for six ganglion cells responding to six stimulation pulses.

Using this approach, a stimulation electrode may be coupled directly to the inductor coil pair, using the train of sine wave pulses that are received directly from the external primary coil inductor to produce a stimulating current that is capable of eliciting action potential in neurons. The stimulation circuit can be used to produce low cost, low power neural stimulators for multiple uses including but not limited to nerve cuff stimulators, deep brain stimulators and retinal prosthesis.

In a preferred embodiment, the integrated nanowire array device may be self-powered by incorporating one or more optoelectronic nanowire batteries, in which one or more nanowire arrays function to accumulate and store charge, taking advantage of the large surface-to-volume ratio of the nanowires and the high quantum efficiency.

These self-powering arrays, referred to herein as "power arrays," may be fabricated on or connected to one or more p-n junctions to produce a voltage drop to provide enhanced storage capacity. Increasing the number of p-n junctions in series will increase the voltage drop, and a bias may be applied based on conditions determined by the device processor. The external source that provides the charge to be collected and stored in the nanowire power array may be in the form of an optical, electrical, chemical, thermal, acoustic, or other stimulus, any combination thereof.

In a retinal implant, the nanowire array(s) used for generating power, i.e., the power array(s), may be incorporated into the phototransductive array without loss of resolution because the density of nanowires greatly exceeds the density required to mimic biological photoreceptors. The "power array" may be one or more separate or additional arrays, or an array may be configured to perform multiple functions, such as both detection within a particular wavelength and charge accumulation for self-powering. In a multi-function configuration, the device processor may be used to allocate array resources according to demand. Alternatively, the power array may be formed as a separate array and connected to the phototransductive array via appropriate interconnection means. The power array may be fabricated to enhance sensitivity within a specific wavelength range, for example, to ensure that the external light energy source is adequate under poorly-lit conditions, or the power array may be fabricated to collect light across the entire range of sensitivity, e.g., 300 nm to 1700 nm, which is much broader than is needed for human vision, thus maximizing the amount of energy available for self-power generation, without spectral limitations as might be imposed on the phototransductive array.

Figure 15:
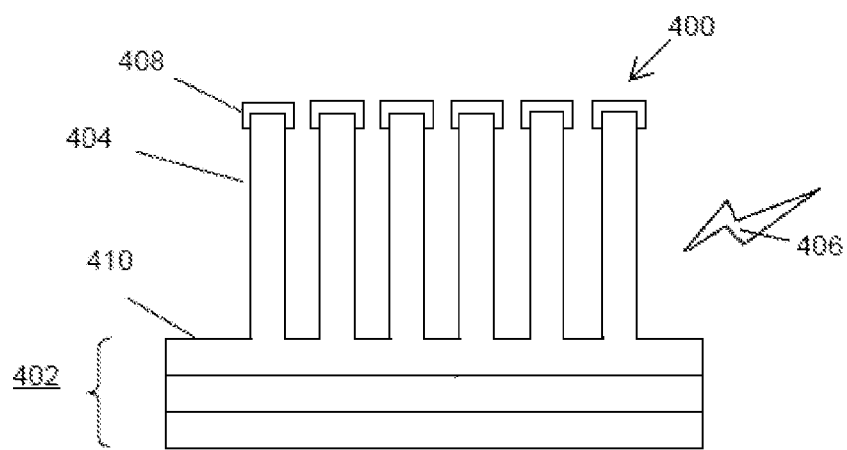
FIG. 15 is a diagrammatic side view of first exemplary embodiment of a self-powering nanowire array.

As shown in FIG. 15, a power array 400 according to the present invention includes a substrate 402 that may include two or more differentially doped layers (alternating p-type and n-type) to define a plurality of p-n junctions. For fabrication, these layers may be formed prior to formation of the nanowire array by using well-known fabrication methods such as epitaxial deposition of alternating p-doped and n-doped silicon layers, finishing with an upper layer of the $p^+/p^-/p^+$ epi structure that may be used to form the nanowire array (as described with reference to FIGS. 7a-7f.)

Referring to FIG. 15, substrate 402 includes alternating layers 402a, 402b, 402c, with upper layer 402a providing the epitaxial layer within which the nanowires will be formed. In this example, the layers are p-type, n-type and p-type, respectively. At the p-n junctions defined by the interfaces between the two layers, e.g., layers 402a and 402b, charge accumulates within the depletion region when energy, e.g., from light, impinges on the nanowire array. The charge will be retained within the respective depletion regions of the p-n junctions until a forward bias voltage exceeding the total voltage drop across all junctions is applied, serving as a gate to release the charge as needed. As an alternative to the formation of the nanowire array on the same substrate within which the p-n junctions are formed, the nanowire array may be fabricated separately and attached to the substrate by appropriate interconnecting means. The nanowire array may detect light 406 along the length of the nanowire, as shown in FIG. 15 as well as on the planar surface of the device 410. While only three layers are illustrated, it will be readily apparent to those of skill in the art that additional layers may be formed, with the total voltage drop, and thus, the total storage capacity, being determined by the number of layers. As described with reference to FIGS. 7a-7f, an insulating material such as PDMS may be formed around the surface of the nanowire array and the substrate to help prevent charge leakage, and may also serve to focus the charge generated. As described previously with reference to FIGS. 8a-8e, a conductive layer 408 may be formed on the tips of the nanowires to define contacts.

Figure 16:
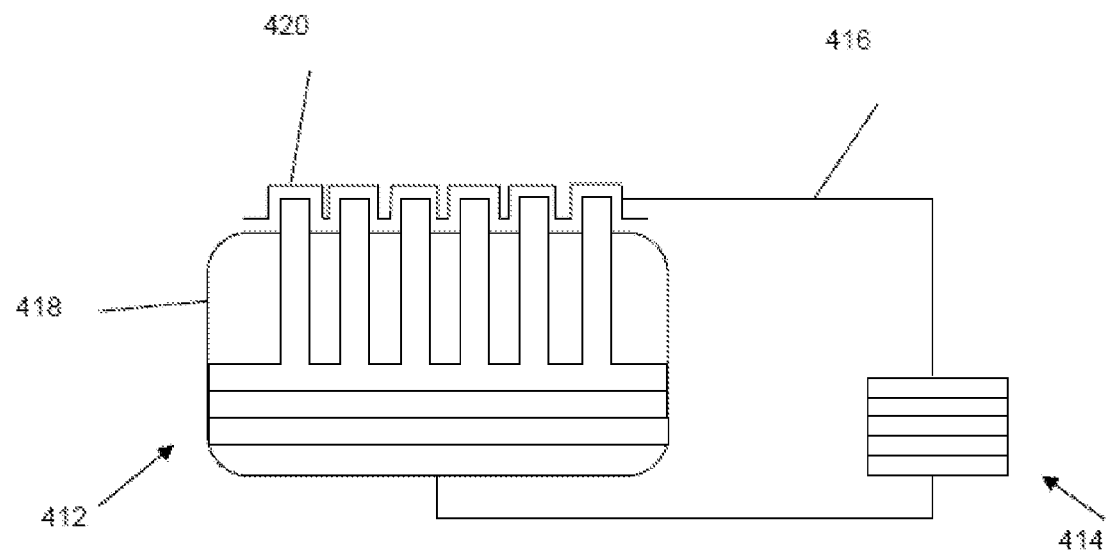
FIG. 16 is a diagrammatic side view of a second exemplary embodiment of a self-powering nanowire array.

FIG. 16 illustrates an alternative embodiment of the self-powering nanowire array in which the power array similar to that shown in FIG. 15 is combined with a separate storage structure. As shown, power array 412 is connected by interconnect 416 to charge collection structure 414, which is formed by a plurality of p-n junctions. The upper surface of storage structure 414 may be capable of collecting energy from an external source and converting it to a charge that accumulates within the depletion regions defined by the p-n junctions. As with the embodiment of FIG. 15, any number of p-n junctions may be formed, with the voltage drop and resulting storage capacity being determined by the number of junctions. Similarly, the bias voltage required to gate the charge will be determined by the number of junctions. As will be readily apparent to those of skill in the art of semiconductor fabrication, the power array 412 and the collection structure 414 may be formed at different locations on the same substrate and interconnected using conventional fabrication methods, or the array and storage structure may be formed on separate substrates and connected using known interconnect methods. Positioning may be selected to optimize efficiency in charge accumulation or may be determined by other design considerations applicable to implanted devices. As in the preceding embodiment, all or part of the assembly may be encased in an insulating material 418, and contacts 420 may be formed on the tips of the nanowires of power array 412 for connection to interconnect 416.

Figure 17:
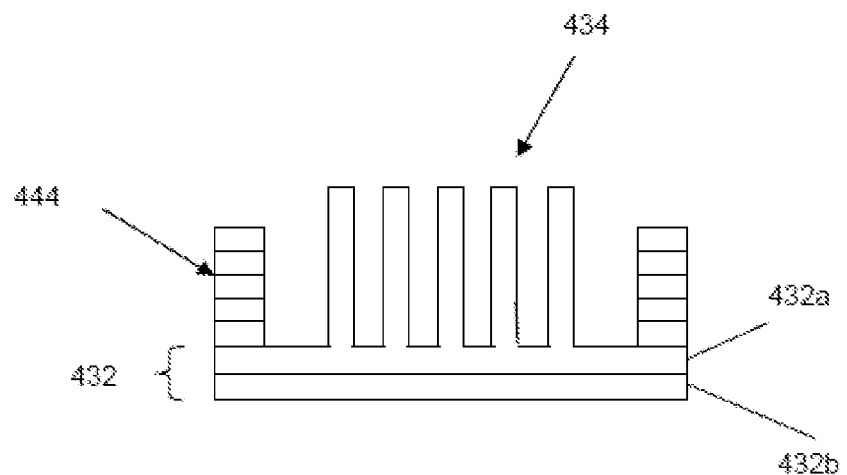
FIG. 17 is a diagrammatic side view of a third exemplary embodiment of a self-powering nanowire array

Another variation of the self-powering device is shown in FIG. 17, in which a nanowire array 434 is formed on the same substrate 432 as one or more charge collection structures 444 comprising a plurality of p-n junctions. (Two charge collection structures 444 are shown, but any number may be included as needed to provide the desired performance.) The nanowire array 434 may be formed within the top layer of the substrate or may be attached to the substrate by appropriate attachment methods. The charge collection structures 444 may be used provide energy to the nanowire array 434 to provide a bias voltage to control operation of the device. A similar function may be performed by replacing charge collection structure(s) 444 with a separate nanowire array which will serve as a power array.

Figures 18A, 18B:
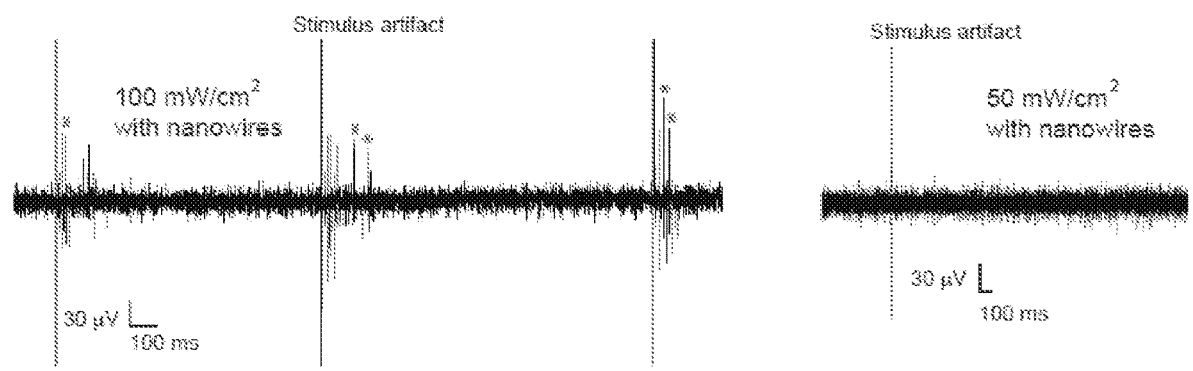
Figure 18C:
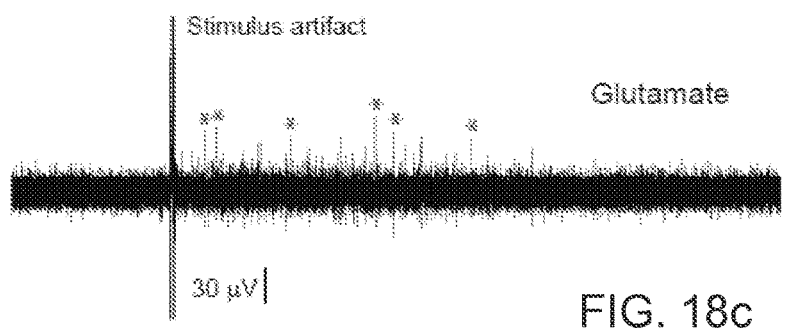
Figure 18D:
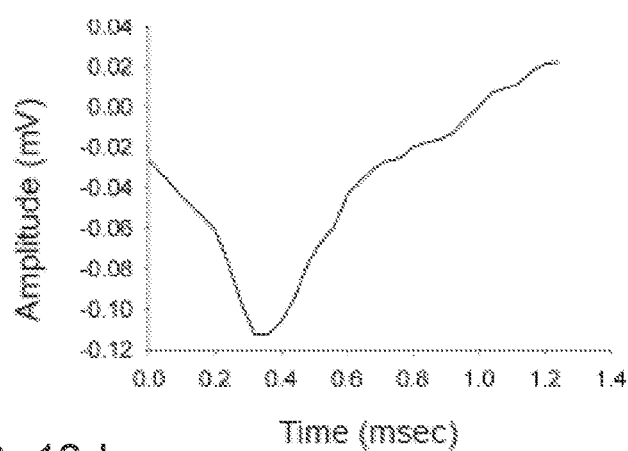
Figure 18E:
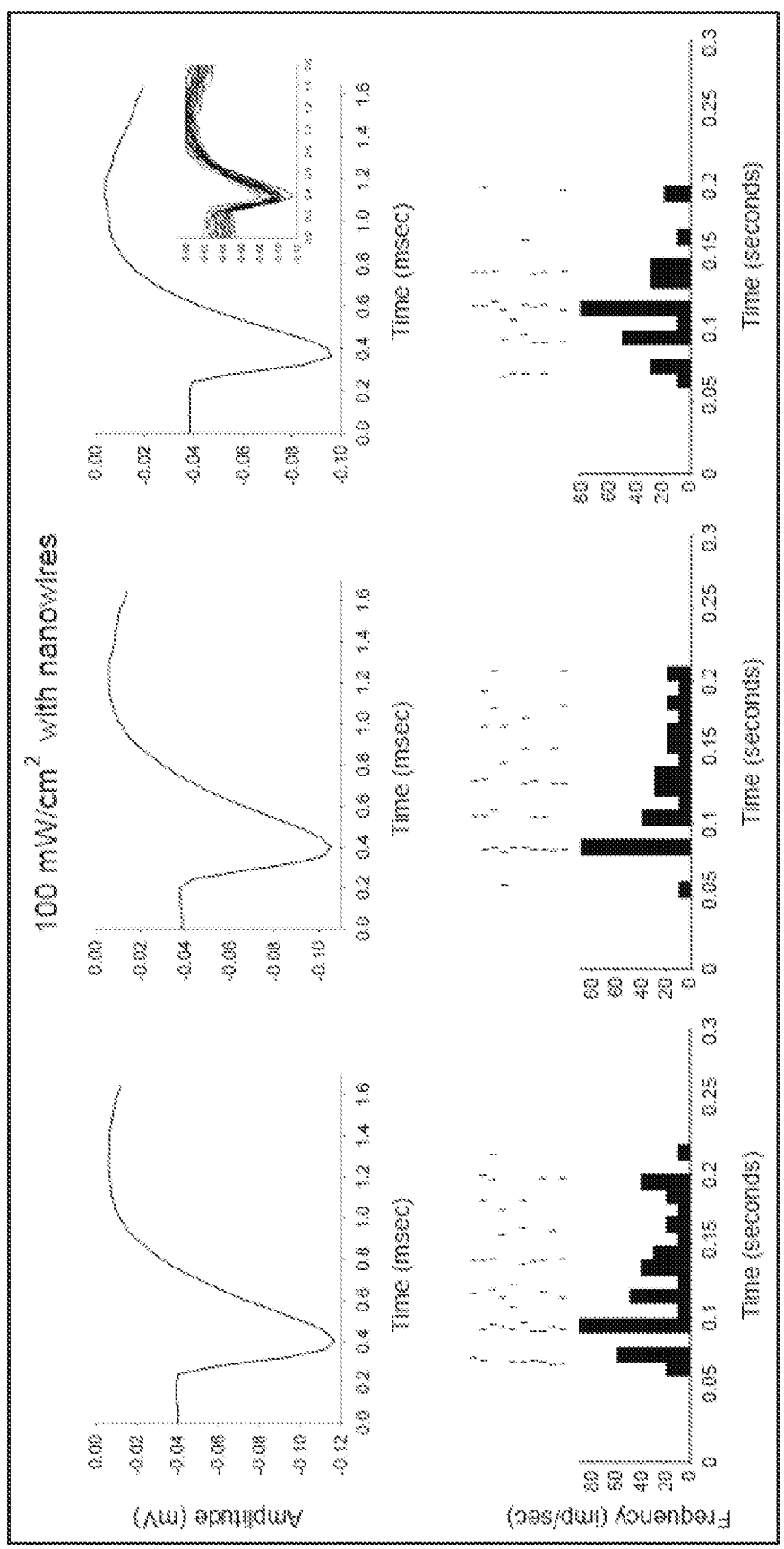
Figure 19A:
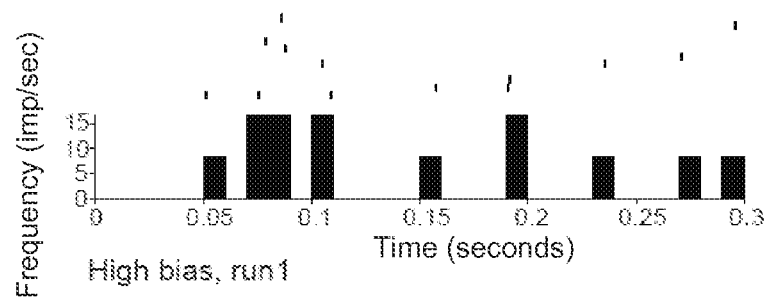
FIGS. 19a-d illustrate a representative high-low-high-low bias stimulation sequence.
Figure 19B:
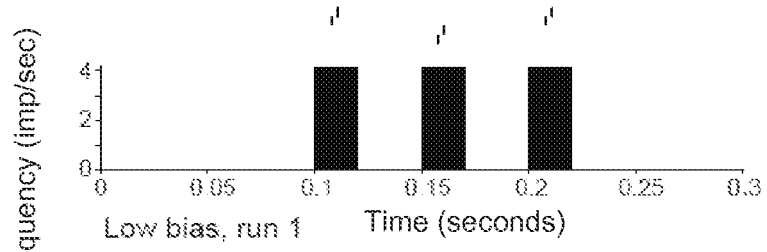
Figure 19C:
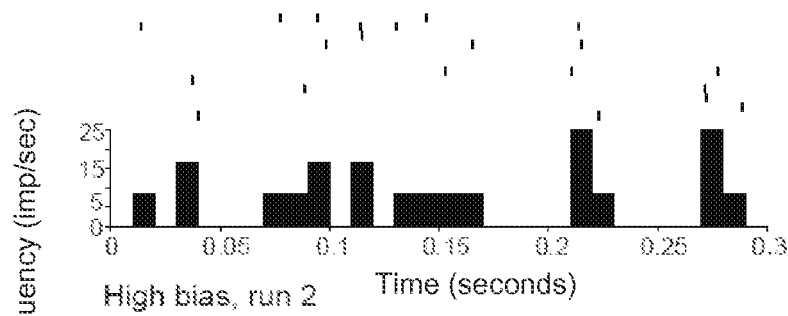
Figure 19D:
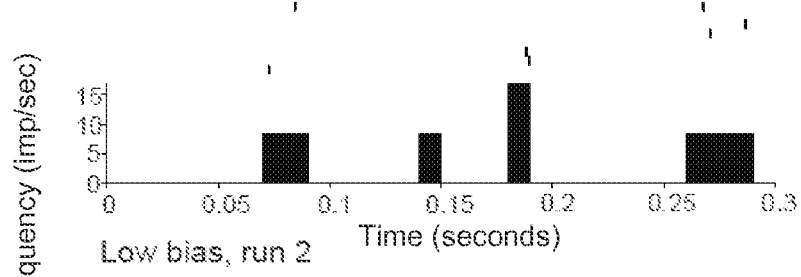

Testing of a nanowire device constructed as described herein was conducted using surgically isolated intact neural sensory retinal explants from wild type Sprague-Dawley rats. Ganglion cell action potentials were measured in response to stimulation by the nanowire devices. Retinas were bleached at 105 lux with full field white light for 20 minutes prior to all experiments, followed by stimulation with 680 nm red light pulsed ten times one second apart. This wavelength of light has been reported to be outside of the rat's visible range, but it is possible that at sufficiently high light intensities some residual response could persist. A number of detailed control studies were conducted to confirm that 680 nm light in combination with the bleaching protocol elicited no ganglion cell activity at 100 mW/cm$^2$. All experiments, including controls, were done in the same preparation during the same experiment in a continuous 20 minute recording session. Ganglion cell responses were recorded on the epiretinal side using a 64 channel multielectrode array (MEA) in response to electrical stimulation by the nanowires placed on the photoreceptor (i.e., subretinal) side following light stimulation of the devices. FIGS. 18a-18h provide the results. FIG. 18a is a ganglion cell voltage trace following full field illumination of the nanowires with a stimulation light intensity on the order of hundreds of milliwatts per square centimeter at 680 nm after bleaching. The asterisks indicate some of the recorded action potentials following the stimulus. Spikes reproducibly occurred following pulsed illumination of the device. No spikes or occasional spontaneous spikes were observed following light stimulation, as shown in the plot of amplitude as a function of time in FIG. 18h. FIG. 18c is the ganglion cell voltage trace for induced pharmacological spiking (indicated by asterisks) following glutamate bath application after prolonged (>20 minutes) recordings. These results suggest that the retina retained the capability for ganglion cell activity. FIG. 18d is an amplitude-time plot showing an averaged (n=14 recorded traces) glutamate single unit. FIG. 18e shows three examples of representative ganglion cell averaged single unit recordings (n=27, 43, and 42 traces from left to right, respectively) and their PSTH (peristimulus time histogram) due to stimulation by the nanowires in response to 100 mW/cm$^2$ illumination. The inset for the right-most plot shows the raw traces that make up the average for the panel. Raw traces were consistently uniform and reproducible across all experiments. FIG. 18*f* shows the PSTH following 100 mW/cm$^2$ illumination in the absence of the nanowire devices. FIG. 18*g* is the PSTH following 50 mW/cm$^2$ illumination of devices. In both cases (FIGS. 18*f* and 18*g*) note the occasional spontaneous action potentials independent of the light stimulus. This suggests that even though the retina was not responding to the 680 nm light at 100 mW/cm$^2$ in the absence of the nanowires (FIG. 18*f*) or 50 mW/cm$^2$ intensity with the nanowires, the retina was able to produce spontaneous spikes. FIG. 18*h* is a plot of the Representative averaged single unit (n=10) for a spontaneous recording at 100 mW/cm$^2$ in the absence of the nanowires. Subretinal electrical stimulation by the nanowire arrays produced robust and reproducible ganglion cell responses with PSTH latencies and firing frequencies comparable to those reported in the literature for indirect electrical stimulation of ganglion cells (FIGS. 18*a* and 18*e*). The nanowires were then tested to determine their ability to reproducibly and reversibly alter and recover the firing rate of stimulated ganglion cells. Retinal explants were subjected to 680 nm light at a stimulation intensity on the order of hundreds of milliwatts per square centimeter following bleaching at two different bias voltages across the nanowire array, 100 and 200 mV. At the higher bias, more current was delivered to the retina for the same light stimulation, producing a higher response frequency from ganglion cells. Experiments consisted of alternating between high and low biases repeatedly over several runs in the same preparation in the same experiment.

FIGS. 19*a*-19*d* show a representative high-low-high-low bias stimulation sequence. The left panels in each figure show the PSTH for each set of data following ten stimulation pulses, with the corresponding raw waveforms for each histogram plotted in the right side panels. There is an obvious qualitative difference in the firing rates between the high and low biases, as expected, with the firing frequency higher at 200 mV. Differences in firing rates were also statistically significant when compared using a paired t-test ($p<0.05$) and a non-parametric Wilcoxon Kruskal-Wallis test (Chi square<0.005). Baseline noise levels for the 100 mV bias measurements were between 60-70 μV, and between 70-85 μV for the 200 mV bias, both well below the 0.5-0.6 mV amplitude ranges of the measured responses. All counted spikes were set to a threshold of three times greater amplitude then the average noise amplitude, ensuring that counted spikes were real.

For controls, we first confirmed in the same experiments that showed positive ganglion cell responses due to 100 mW/cm2 stimulation (FIGS. 18*a* and 18*e*) that currents produced by the nanowires below subthreshold stimulation conditions at 50 mW/cm$^2$ (i.e., 50% of the minimal threshold light intensity at zero device bias) did not cause ganglion cells to fire (FIGS. 18*b* and 18*g*). When the devices were physically removed, 680 nm light at hundreds of mW/cm2 and higher intensities elicited no ganglion cell responses following light stimulation (FIGS. 18*f* and 18*h*). In both types of control experiments (stimulation intensities on the order of hundreds of milliwatts per square centimeter) occasional sparse spontaneous responses were measured during continuous recordings with latencies longer than two times the shortest latency periods at similar intensities, indicating that even though the retina was not responding to the 680 nm light, it remained capable of ganglion cell activity (FIGS. 18*f*-18*h*). Furthermore, following a period of at least 20 minutes of stimulation by the devices and recordings by the MEA, when the devices were removed and in the absence of any light, ganglion cells became quiet, as expected, but immediately responded robustly following bath application of glutamate, the endogenous excitatory neurotransmitter that causes these cells to fire (FIGS. 18*c* and 18*d*). This suggests that following extended periods of stimulation by the nanowires, the retina retains the capability for ganglion cell activity.

The integrated nanowire array devices described herein can exceed the aspect ratio of biological photoreceptors, with each individual nanowire acting as a potential single phototransduction and stimulation element. Further, because their electrical output inherently scales as a function of the incident light and device bias, the nanowires do not need to be individually addressed. Ultimately, this allows the stimulation density of the nanowires to be equivalent to their photosensing resolution. Such a device could in principle be able to use its full density to convey sensory information to the brain at a resolution that exceeds the normal biological resolution of native photoreceptor neurons, should such a property be desired or necessary. If appropriate though, nanowire arrays could also be coupled to downstream integrated circuitry to further modulate the light induced electrical output, similar to the way native light adaptation in the human visual system is achieved across multiple stages throughout the visual pathways, beginning in the photoreceptors themselves.

The nanowire platform of the present invention may be used as an interface and potential prosthesis to generate a nanoscale molecular signaling cue or stimulation based on electric currents for the induction of chemically secreted neuroprotective factors from cells, i.e., not just neurons, but glial cells and other central and peripheral nervous system cells.

In one example, nanowire arrays may be engineered into a broader device to act as an electrical-to-chemical transducer in the development of a nanoengineered artificial chemical synapse. The nanowires may be configured to respond to light or some other input signal. In response to detection of such an input, the array may use its electrical properties to trigger the release of chemically-based signaling molecules, such as various classes of neurotransmitters (e.g., peptides or catecholamines) from a thin film, polymer, or other synthetically engineered material. In one example, a synthetic neurotransmitter may encapsulated within cells or layers in a membrane formed from an electroactive polymer into which the nanowire electrodes extend. The membrane, when activated, opens the cells (or pores in the layers) for a sufficient duration to release the appropriate quantity of the neurotransmitter to effect the desired change. The released molecules can then chemically stimulate and signal neurons, thus inducing or mimicking synaptic behaviors. Nanowire-based devices of this type may be useful for treatment of a wide range of conditions involving synaptic dysfunction or failure, including but not limited to, depression, Alzheimer's disease, Parkinson's disease, and may even be useful in treating drug addiction and some forms of paralysis.

In addition to its application as a retinal prosthesis, the molecular scale of the inventive nanowire platform makes it broadly applicable as an interface and potential prosthesis for other sensory systems and non-sensory parts of the brain and central nervous system.

In addition to its use in retinal implants, the integrated nanowire array device may be used as an optical sensor, e.g., a camera, with a sensitivity comparable to the best CMOS or CCD cameras but at a resolution one to two orders of magnitude better than existing CMOS or CCD cameras for any given light sensitive area. This would represent a significant advance in CMOS or CCD cameras, in which the sensitivity of the sensor size is limited by reduced quantum efficiency as a function of a decreasing photon capture area. Fundamental factors constrain the sensor performance of current semiconductor-based optical devices including the absorption length in silicon, the efficiency of photon absorption (which is very high, typically 40-50% for modern digital cameras), and electron charge density in the silicon. Blue wavelength photons have shorter absorption lengths in silicon than red or green photons. Some of the major factors that limit the maximum number electrons captured by a semiconductor image sensor are the absorption length and electron densities. The wavelength-variable absorption lengths in silicon are exploited in the development of the FOVEON® sensor (Foveon, Inc., Santa Clara, Calif.) and some Sigma digital cameras (Sigma Corporation, Kanagawa, Japan) for example, allowing a single spatial pixel to separate red green and blue colors. Still, the absorption lengths overlap too much for fine wavelength discrimination. Table 2 shows the absorption lengths in silicon.

TABLE 2

| Wavelength (Å) | Color | Absorption (1/e) Length in Silicon (μm) |
|---|---|---|
| 4000 | ~violet | 0.19 |
| 4500 | ~blue | 1.0 |
| 5000 | ~blue-green | 2.3 |
| 5500 | ~green-yellow | 3.3 |
| 6000 | ~orange | 5.0 |
| 6500 | ~red | 7.6 |
| 7000 | ~red limit | 8.5 |

The absorption lengths of photons in Table 2 are the 1/e depth (e=2.7183), or the 63% probability of a photon being absorbed along that length. Some photons can in reality travel several times this distance before being absorbed. These absorption lengths impact performance as pixels become smaller. For example, small sensor digital cameras currently have pixels smaller than 2 microns. If the absorbed photon results in an electron in the conduction band, it could contribute to photons several pixels away from the target pixel. If the absorbed photon results in an electron in the conduction band, it likely contributes to photons several pixels away from the target pixel. As a result, camera sensitivity is limited.

The integrated optoelectronic nanowires also single photon sensitivity but at much smaller sizes than the noise and sensitivity per sensor and at a higher densities of nanowires per area compared to current microchips. Therefore, the resolution possible with the integrated nanowires arrays is much greater at the same sensitivity. For example, an integrated array with nanowire sensors may have 250 nm vs. 2000 nm as is found in digital SLR cameras, representing around 100 times better resolution for the same sensor area, with same sensitivity and low signal to noise ratio, as full frame digital SLR cameras.

REFERENCES (INCORPORATED HEREIN BY REFERENCE)

1) Kim, H., et al., "Fabrication of Vertical Silicon Nanowire Photodetector Arrays using Nanoimprint Lithography", *Proceedings of SPIE*, 2010, pp. 7591-7595.
2) Soci, C., et al., "ZnO Nanowire UV Photodetectors with High Internal Gain", *Nano Letters,* 2007, Vol. 7, p. 1003.
3) Zhang, A., et al., "Silicon Nanowire Detectors Showing Phototransistive Gain", *Applied Physics Letters,* 2008, Vol. 93, 121110-1-3.
4) Khraiche, M. L., N. Jackson, and J. Muthuswamy. Biology Society, 2009. EMBC 2009. Annual International Conference of the IEEE, 2009.
5) Humayun, M. S., et al., "Visual perception in a blind subject with a chronic microelectronic retinal prosthesis", *Vision Res.,* 2003, 43(24), pp. 2573-2581.
6) Winter, J. O., et al., "Retinal prostheses: current challenges and future outlook", *Journal of Biomaterials Science. Polymer Edition,* 2007, 18, pp. 1031-1055.
7) Besch, D., et al., "Extraocular surgery for implantation of an active subretinal visual prosthesis with external connections: feasibility and outcome in seven patients", *Br. J. Ophthalmol,* 2008, 92(10): p. 1361-8.
8) Zhang, A., et al., "Nanowire Photodetectors", *Journal of Nanoscience and Nanotechnology,* 2010, 10: p. 1430-1449.
9) Zhang, A., et al., "Characterization and physics of top-down silicon nanowire phototransistors", *Proceedings of SPIE,* 2010, 7608, p. 76081D-8.
10) Sun, K., et al., "Compound Semiconductor Nanowire Solar Cells" *Selected Topics in Quantum Electronics, IEEE Journal of,* 2010. PP(99): p. 1-17.
11) Soci, C., et al., Nanowire Photodetectors. *Journal of Nanoscience and Nanotechnology,* 2010, 10(3): p. 1439-1449.
12) Curcio, C. A., et al., "Human photoreceptor topography", *J Comp Neurol,* 1990, 292(4): p. 497-523.
13) Friedburg, C., M. M. Thomas, and T. D. Lamb, "Time course of the flash response of dark- and light-adapted human rod photoreceptors derived from the electroretinogram", *J Physiol,* 2001. 534(Pt 1): p. 217-42.
14) Palanker, D., et al., "Design of a high-resolution optoelectronic retinal prosthesis", *J Neural Eng,* 2005, 2(1): p. S105-20

The invention claimed is:

1. An integrated nanowire device, comprising:
  a first array of semiconductor nanowires having a first quantum efficiency and a first set of characteristics, wherein the first set of characteristics are selected from the group consisting of doping, spatial distribution, quantity, density, pitch, diameter, length and shape, and wherein the first array is configured to generate a first plurality of charges in response to electromagnetic energy impinging thereon;
  at least one second array of semiconductor nanowires having a second quantum efficiency and one or more second sets of characteristics different from the first set of characteristics, the at least one second array configured to perform one or more of generating a stimulation current, detecting a localized response to stimulation, and generating power;
  an integrated circuit comprising a processor in electrical communication with the first array of semiconductor nanowires and the at least one second array of semiconductor nanowires, wherein the processor is configured to receive the first plurality of charges and generate a processor signal therefrom; and
  a power source.

2. The integrated nanowire device of claim 1, wherein the at least one second array of semiconductor nanowires is configured to produce a stimulation current in response to the processor signal.

3. The integrated nanowire device of claim 1, wherein the at least one second array of semiconductor nanowires comprises two arrays, wherein one of the two arrays is configured to produce a stimulation current in response to the processor signal and the second of the two arrays is adapted to detect a localized response to the stimulation current and provide feedback to the processor.

4. The integrated nanowire device of claim 3, wherein the processor is programmed to execute an algorithm for receiving the feedback and adjusting the stimulation current based on the localized response.

5. The integrated nanowire device of claim 4, wherein the device is a retinal implant and the algorithm is based on a model for predicting retinal ganglion cell responses.

6. The integrated nanowire device of claim 5, wherein the model is a generalized linear model.

7. The integrated nanowire device of claim 1, wherein the first set of characteristics is configured to respond to a first wavelength range and the one or more second sets of characteristics are adapted to respond to at least one second wavelength range.

8. The integrated nanowire device of claim 7, wherein the at least one second wavelength range comprises two different wavelength ranges, wherein the first wavelength range corresponds to a red light range and the two different wavelength ranges correspond to a green light range and a blue light range.

9. The integrated nanowire device of claim 7, wherein the first wavelength range is from 350 nm to 1100 nm and the at least one second wavelength range is a smaller range within the first wavelength range.

10. The integrated nanowire device of claim 1, wherein the first set of characteristics is adapted to produce the first plurality of charges with a first quantum efficiency and the one or more second sets of characteristics are configured to produce a second plurality of charges with one or more second quantum efficiencies.

11. The integrated nanowire device of claim 1, wherein one or more of the first array of nanowires, the at least one second array of semiconductor nanowires, and the processor are disposed on at least one flexible substrate comprising a biocompatible material.

12. The integrated nanowire device of claim 11, wherein the biocompatible material is poly(p-xylylene) or polydimethylsiloxane.

13. The integrated nanowire device of claim 1, wherein the at least one second array of semiconductor nanowires comprises a power array configured to act as the power source.

14. The integrated nanowire device of claim 13, wherein the power array is fabricated on or in electrical communication with a substrate comprising one or more p-n-junctions, wherein each p-n junction comprises a voltage drop configured to accumulate charges for operation of the device.

15. The integrated nanowire device of claim 14, wherein a surface of a separate substrate is configured to collect energy from an external energy source and generate charges therefrom.

16. The integrated nanowire device of claim 1, wherein the device is an implant and the power source comprises:
 a first inductive coil disposed adjacent to an implant site; and
 a second inductive coil disposed external to the implant site for inducing a magnetic field at the first inductive coil.

17. The integrated nanowire device of claim 16, wherein the first inductive coil is connected in parallel with a capacitor to define a LC resonant tank that is further connected to a diode for generating a stimulation current.

18. An integrated nanowire device, comprising:
 one or more first semiconductor nanowire arrays having a first quantum efficiency and a first set of characteristics selected for peak responsivity within at least one first wavelength range, wherein the first set of characteristics are selected from the group consisting of doping, spatial distribution, quantity, density, pitch, diameter, length and shape, and wherein the one or more first nanowire arrays are configured to generate a first plurality of charges in response to an external electromagnetic energy impinging thereon;
 one or more second semiconductor nanowire arrays having one or more second quantum efficiency and one or more second sets of characteristics different from the first set of characteristics, the one or more second nanowire arrays configured to generate a stimulation current;
 an integrated circuit comprising a processor in electrical communication with the one or more first nanowires and the one or more second nanowires, wherein the processor is configured to receive the first plurality of charges and generate a processor signal therefrom to control generation of the stimulation current; and
 a power source.

19. The integrated nanowire device of claim 18, further comprising one or more third semiconductor nanowire arrays disposed in close proximity to the one or more second nanowire arrays, wherein the one or more third semiconductor nanowire arrays are configured to detect a localized response to the stimulation current and provide feedback to the processor, wherein the processor is programmed to execute an algorithm for receiving the feedback and adjusting the stimulation current based on the localized response.

* * * * *